US012694981B2

(12) United States Patent
Virmani et al.

(10) Patent No.: US 12,694,981 B2
(45) Date of Patent: Jul. 28, 2026

---

(54) MULTI-VARIABLE HEATMAPS FOR COMPUTER-AIDED DIAGNOSTIC MODELS

(71) Applicant: Verily Life Sciences LLC, Mountain View, CA (US)

(72) Inventors: Sunny Virmani, Fremont, CA (US); Peter Mark Wubbels, Redwood City, CA (US); Jinhua Xu, Redwood City, CA (US)

(73) Assignee: Verily Health Inc., Dallas, TX (US)

( * ) Notice: Subject to any disclaimer, the term of this patent is extended or adjusted under 35 U.S.C. 154(b) by 601 days.

(21) Appl. No.: 17/773,149

(22) PCT Filed: Oct. 29, 2020

(86) PCT No.: PCT/US2020/058001
§ 371 (c)(1),
(2) Date: Apr. 29, 2022

(87) PCT Pub. No.: WO2021/087140
PCT Pub. Date: May 6, 2021

(65) Prior Publication Data
US 2022/0375610 A1     Nov. 24, 2022

Related U.S. Application Data

(60) Provisional application No. 62/927,434, filed on Oct. 29, 2019, provisional application No. 62/927,426, (Continued)

(51) Int. Cl.
| | |
|---|---|
| G16H 50/20 | (2018.01) |
| G06T 7/00 | (2017.01) |
| G16H 30/20 | (2018.01) |

(52) U.S. Cl.
CPC ........... G16H 50/20 (2018.01); G06T 7/0012 (2013.01); G16H 30/20 (2018.01); *G06T 2207/20084* (2013.01); *G06T 2207/30041* (2013.01)

(58) Field of Classification Search
CPC ...... G16H 50/20; G16H 30/20; G06T 7/0012; G06T 2207/20084; G06T 2207/30041
See application file for complete search history.

(56) References Cited

U.S. PATENT DOCUMENTS

| | | | | |
|---|---|---|---|---|
| 7,298,883 | B2 * | 11/2007 | Giger ................. | G06F 18/2321 |
| | | | | 600/443 |
| 8,098,907 | B2 * | 1/2012 | Yan ...................... | G06T 7/0012 |
| | | | | 382/128 |

(Continued)

OTHER PUBLICATIONS

Cristina Gonzalez-Gonzalo, Iterative augmentation of visual evidence for weakly-supervised lesion localization in deep interpretability frameworks (Year: 2019).*

(Continued)

*Primary Examiner* — Stephen S Hong
*Assistant Examiner* — Carl E Barnes, Jr.
(74) *Attorney, Agent, or Firm* — Perkins Coie LLP

(57) ABSTRACT

Introduced here are diagnostic platforms able to produce visualizations that visually highlight the pixels considered as evidence of a medical condition by a computer-aided diagnostic (CADx) model. A CADx model may be based on, for example, a multi-headed neural network designed to detect the presence/progression of multiple medical conditions. By explaining how each output is produced by the multi-headed neural network, a diagnostic platform can identify the latent variable (s) responsible for producing each output. For example, a diagnostic platform may create a multi-variable heatmap that visually distinguishes the pixels considered as evidence of each multiple condition by a multi-headed (Continued)

neural network. To accomplish this, the diagnostic platform may create multiple heatmaps by producing, for each output, a separate heatmap that distinguishes the pixels in the image considered as evidence of the corresponding medical condition by the multi-headed neural network, and then compiling the multiple heatmaps into the multi-variable heatmap.

20 Claims, 27 Drawing Sheets

Related U.S. Application Data filed on Oct. 29, 2019, provisional application No. 62/927,415, filed on Oct. 29, 2019.

(56)                   References Cited

U.S. PATENT DOCUMENTS

| | | | | |
|---|---|---|---|---|
| 8,879,813 | B1 * | 11/2014 | Solanki | G06T 7/0016 |
| | | | | 382/128 |
| 10,430,946 | B1 * | 10/2019 | Zhou | A61B 5/02007 |
| 10,599,984 | B1 * | 3/2020 | Wubbels | G16H 50/20 |
| 10,610,098 | B1 * | 4/2020 | Soliz | G06V 40/197 |
| 10,810,512 | B1 * | 10/2020 | Wubbels | G06N 20/00 |
| 11,288,800 | B1 * | 3/2022 | Najmi | G06T 11/206 |
| 2014/0314288 | A1 * | 10/2014 | Roychowdhury | G06T 7/0012 |
| | | | | 382/128 |
| 2015/0265144 | A1 * | 9/2015 | Burlina | G06T 7/0012 |
| | | | | 351/246 |
| 2016/0278743 | A1 * | 9/2016 | Kawashima | G16H 10/40 |
| 2017/0209579 | A1 * | 7/2017 | Curley | A61K 41/0052 |
| 2018/0165810 | A1 * | 6/2018 | Jia | G16H 30/40 |
| 2019/0043193 | A1 * | 2/2019 | Odaibo | G06F 18/285 |
| 2019/0096060 | A1 * | 3/2019 | Zhang | G06T 7/0014 |
| 2019/0110753 | A1 * | 4/2019 | Zhang | A61B 3/0025 |
| 2019/0114771 | A1 * | 4/2019 | Zhang | A61B 3/14 |
| 2020/0069175 | A1 * | 3/2020 | Kumagai | A61B 3/0025 |
| 2020/0178794 | A1 * | 6/2020 | El-Baz | A61B 3/1241 |
| 2020/0202529 | A1 * | 6/2020 | Hart | A61B 3/0025 |

OTHER PUBLICATIONS

C. Lam, Automated Detection of Diabetic Retinopathy using Deep Learning (Year: 2016).*

R.F. Mansour, Deep-learning-based automatic computer-aided diagnosis system for diabetic retinopathy (Year: 2017).*

S. Roychowdhury, DREAM Diabetic Retinopathy Analysis Using Machine Learning (Year: 2014).*

H. Li, EnsembleNET, End-to-End optimization of Multi-headed models (Year: 2019).*

R. Sayres, Using a Deep Learning Algorithm and Integrated Gradients Explanation to Assist Grading for Diabetic Retinopathy (Year: 2019).*

N. Chakrabarty, A Deep Learning Method for the detection of Diabetic Retinopathy (Year: 2018).*

R, Gargeya, Automated Identification of Diabetic Retinopathy Using Deep Learning (Year: 2017).*

Mukund Sundararajan Axiomatic Attribution for Deep Networks (Year: 2017).*

Maimoona K., CAD-EYE: An Automated System for Multi-Eye Disease Classification Using Feature Fusion with Deep Learning Models and Fluorescence Imaging for Enhanced Interpretability (Year: 2024).*

Anonymous, "What is a Multi-Headed Model? And What Exactly is a 'Head' in a Model?", May 6, 2019, https://stackoverflow.com/questions/56004483/what-is-a-multi-headed-model-and-what-exactly-is-a-head-in-a-model.

Gonzalez-Gonzalo et al., "Iterative Augmentation of Visual Evidence for Weakly-Supervised Lesion Localization in Deep Interpretability Frameworks", arxiv.org, Oct. 16, 2019, 13 pages.

International Search Report for Application No. PCT/US2020/058001, mailed on Mar. 26, 2021, 4 pages.

* cited by examiner

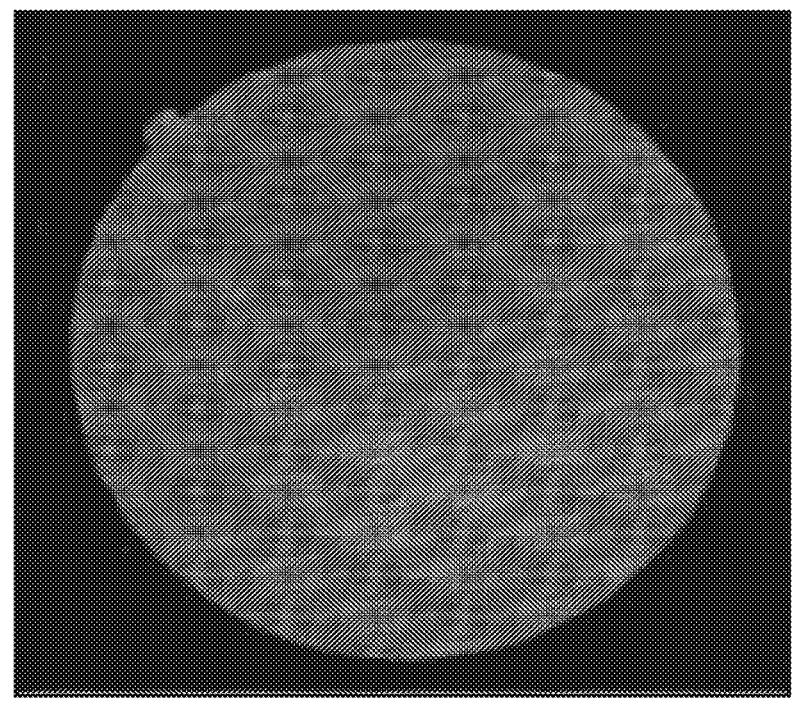
FIG. 5B
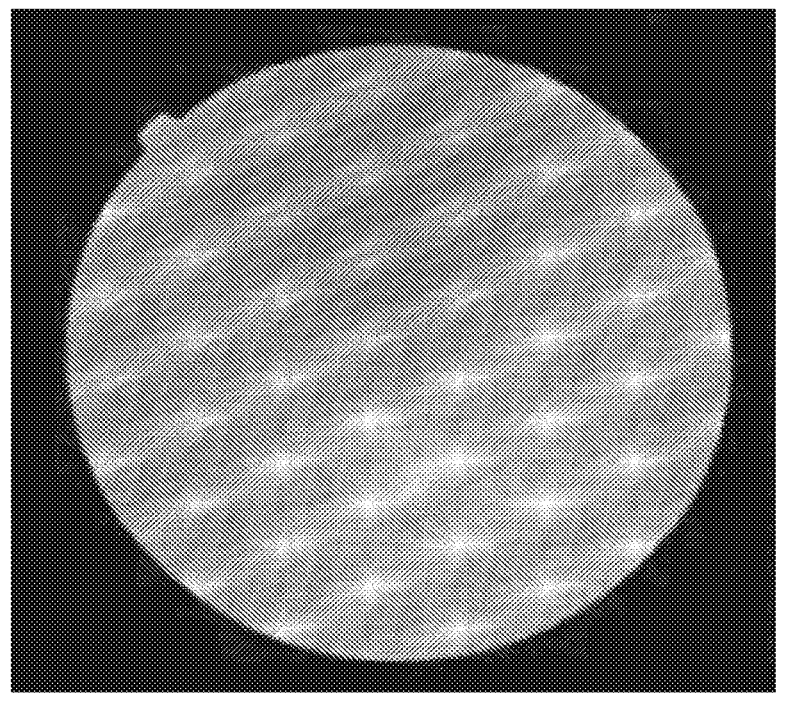
FIG. 5A

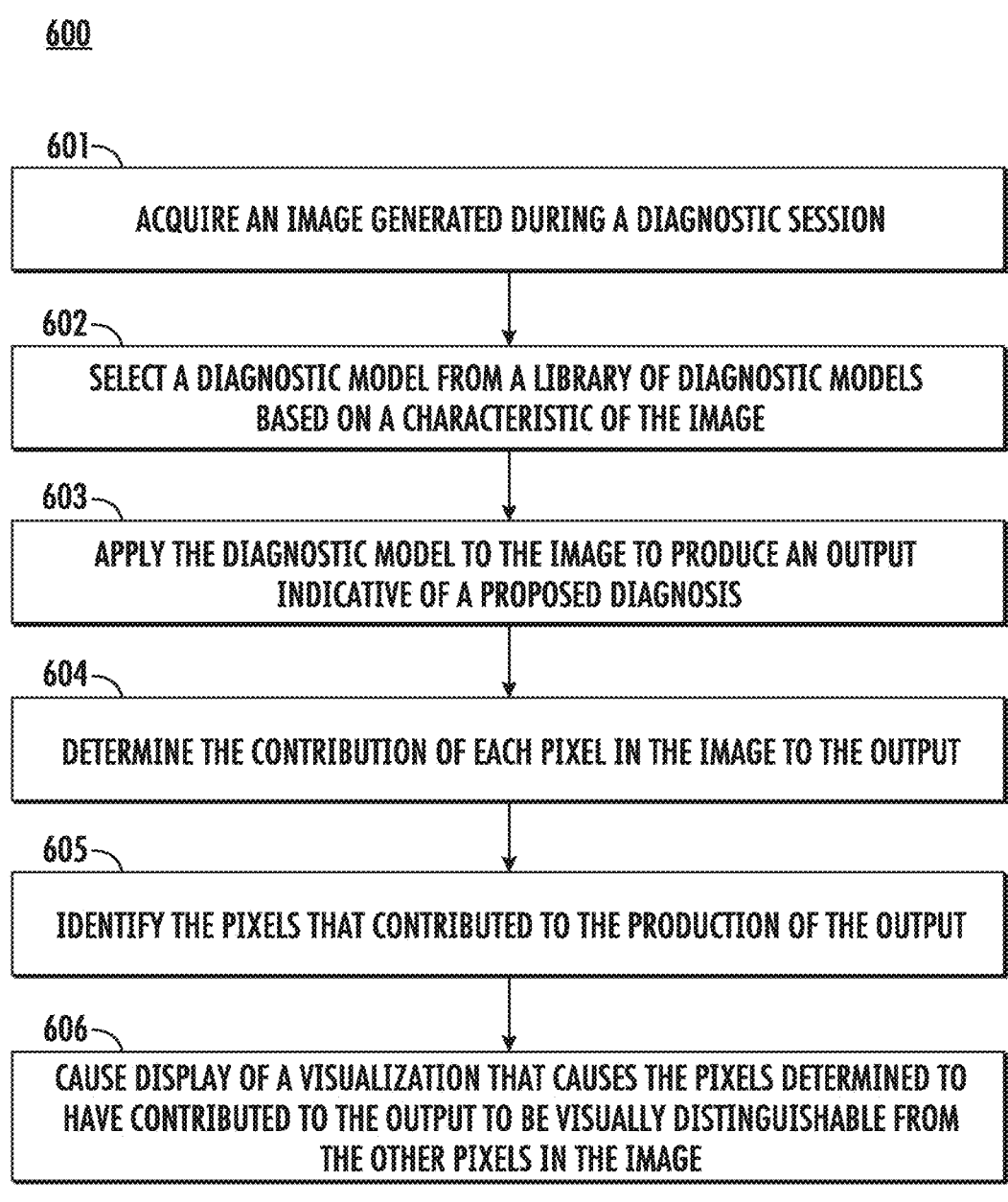

600

601 ── ACQUIRE AN IMAGE GENERATED DURING A DIAGNOSTIC SESSION

602 ── SELECT A DIAGNOSTIC MODEL FROM A LIBRARY OF DIAGNOSTIC MODELS
BASED ON A CHARACTERISTIC OF THE IMAGE

603 ── APPLY THE DIAGNOSTIC MODEL TO THE IMAGE TO PRODUCE AN OUTPUT
INDICATIVE OF A PROPOSED DIAGNOSIS

604 ── DETERMINE THE CONTRIBUTION OF EACH PIXEL IN THE IMAGE TO THE OUTPUT

605 ── IDENTIFY THE PIXELS THAT CONTRIBUTED TO THE PRODUCTION OF THE OUTPUT

606 ── CAUSE DISPLAY OF A VISUALIZATION THAT CAUSES THE PIXELS DETERMINED TO
HAVE CONTRIBUTED TO THE OUTPUT TO BE VISUALLY DISTINGUISHABLE FROM
THE OTHER PIXELS IN THE IMAGE

FIG. 6

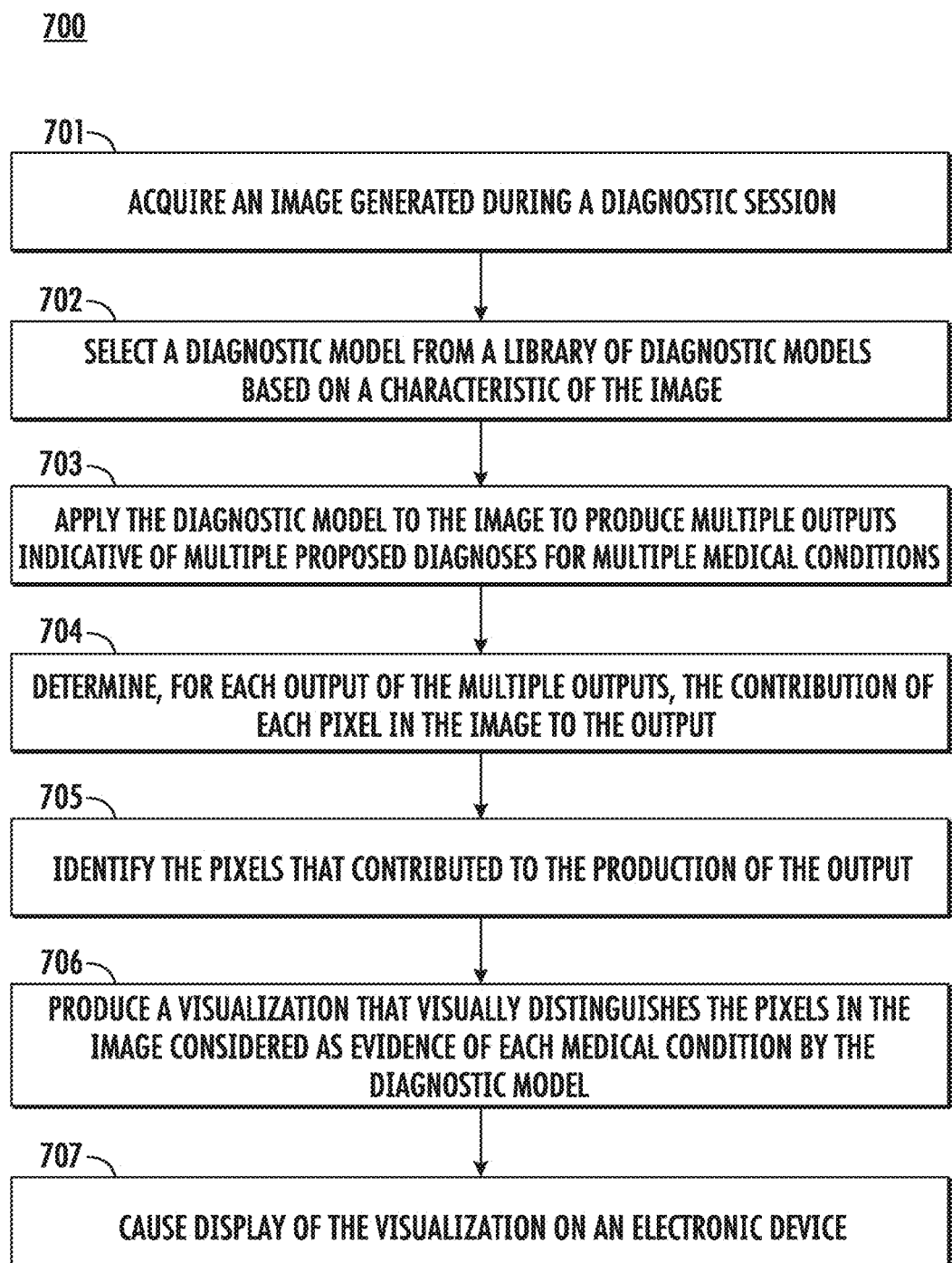

700

701 — ACQUIRE AN IMAGE GENERATED DURING A DIAGNOSTIC SESSION

702 — SELECT A DIAGNOSTIC MODEL FROM A LIBRARY OF DIAGNOSTIC MODELS BASED ON A CHARACTERISTIC OF THE IMAGE

703 — APPLY THE DIAGNOSTIC MODEL TO THE IMAGE TO PRODUCE MULTIPLE OUTPUTS INDICATIVE OF MULTIPLE PROPOSED DIAGNOSES FOR MULTIPLE MEDICAL CONDITIONS

704 — DETERMINE, FOR EACH OUTPUT OF THE MULTIPLE OUTPUTS, THE CONTRIBUTION OF EACH PIXEL IN THE IMAGE TO THE OUTPUT

705 — IDENTIFY THE PIXELS THAT CONTRIBUTED TO THE PRODUCTION OF THE OUTPUT

706 — PRODUCE A VISUALIZATION THAT VISUALLY DISTINGUISHES THE PIXELS IN THE IMAGE CONSIDERED AS EVIDENCE OF EACH MEDICAL CONDITION BY THE DIAGNOSTIC MODEL

707 — CAUSE DISPLAY OF THE VISUALIZATION ON AN ELECTRONIC DEVICE

FIG. 7

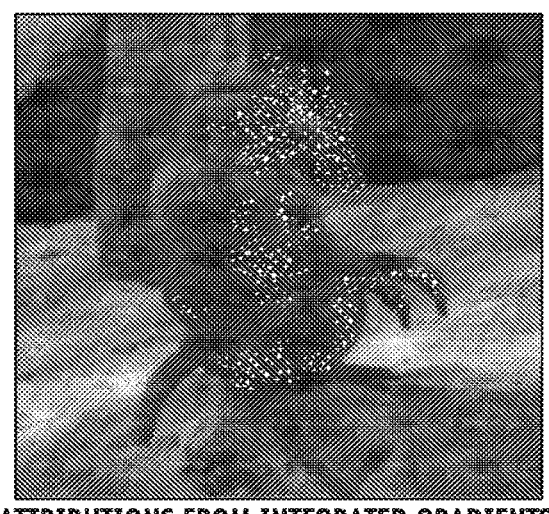
ATTRIBUTIONS FROM INTEGRATED GRADIENTS
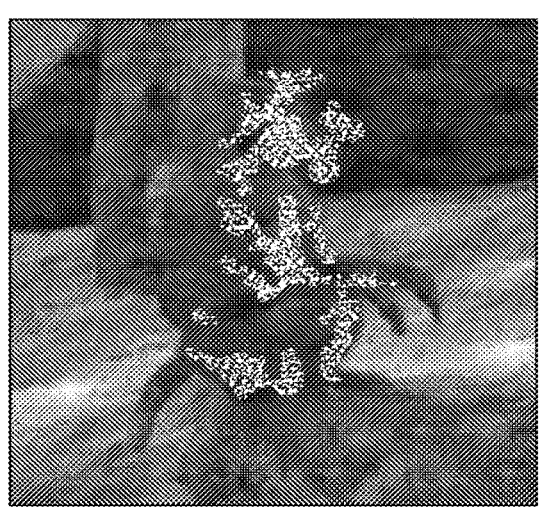
WITH MORPHOLOGICAL OPERATIONS APPLIED
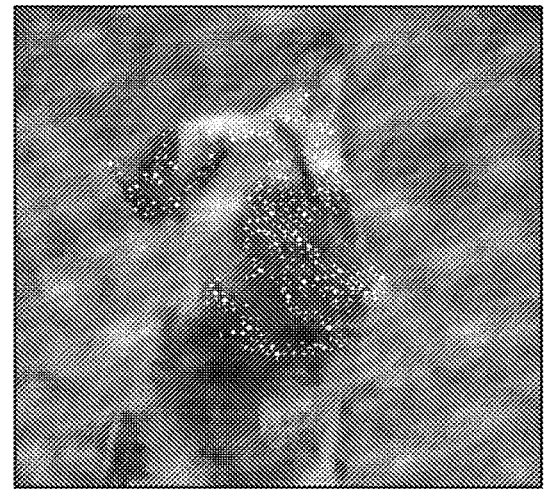
ATTRIBUTIONS FROM INTEGRATED GRADIENTS
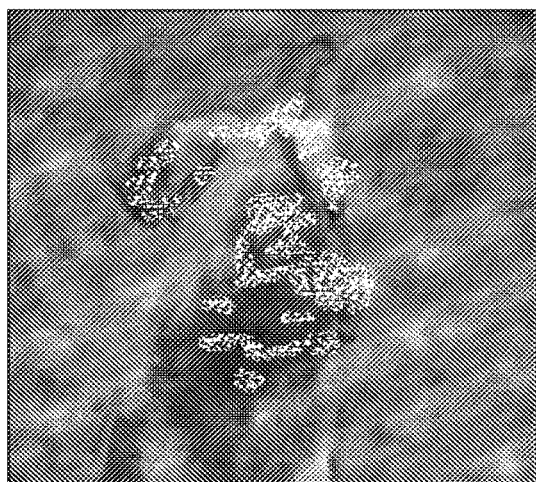
WITH MORPHOLOGICAL OPERATIONS APPLIED
FIG. 12

APPLY ATTRIBUTION MODEL TO PREDICTION GENERATED BY NEURAL NETWORK

↓

EXAMINE MATRIX OF ATTRIBUTION VALUES GENERATED BY ATTRIBUTION MODEL TO IDENTIFY PIXELS HAVING AN ATTRIBUTION VALUES THAT EXCEED A SPECIFIED THRESHOLD

↓

CREATE A VISUALIZATION THAT VISUALLY HIGHLIGHTS THE IDENTIFIED PIXELS

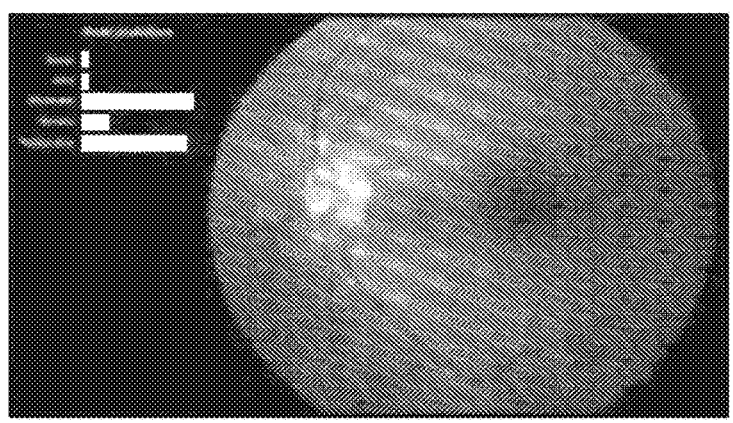

PREDICTION FOR DIABETIC RETINOPATHY SEVERITY

| .01 | .04 | .04 | .08 | .03 |
|-----|-----|-----|-----|-----|
| .01 | .01 | .05 | .07 | .06 |
| .04 | .04 | .04 | .04 | .04 |
| .05 | .05 | .04 | .03 | .03 |
| .05 | .04 | .04 | .04 | .03 |

• • •

⋮

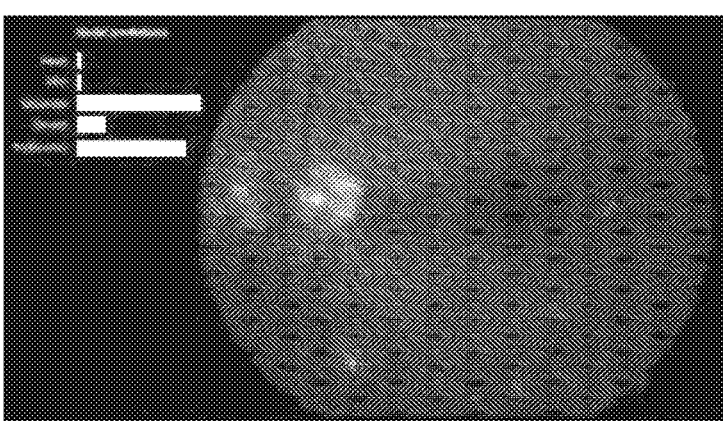

HIGHLIGHTS OF PIXELS DEEMED RELEVANT TO PREDICTION

FIG. 13

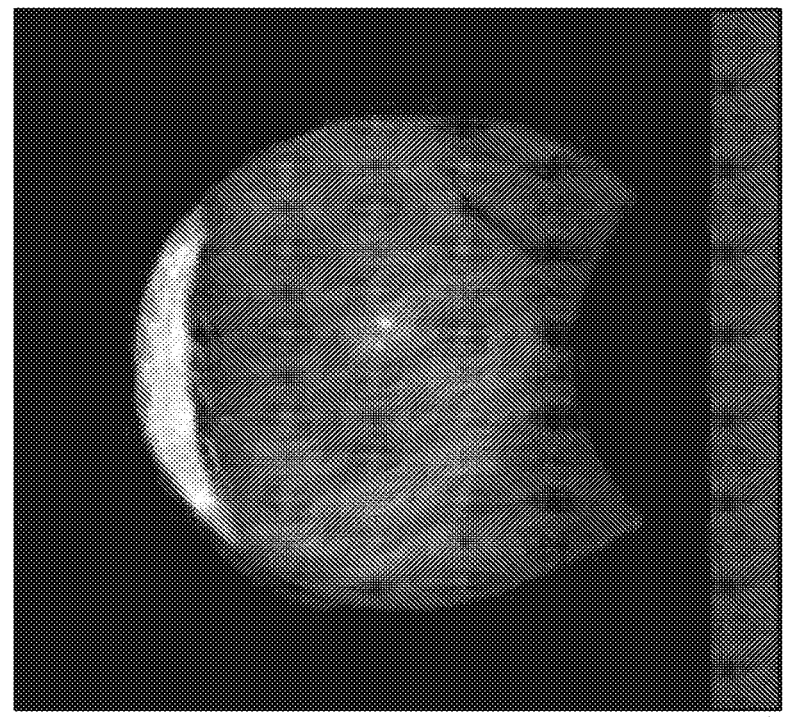
FIG. 14D
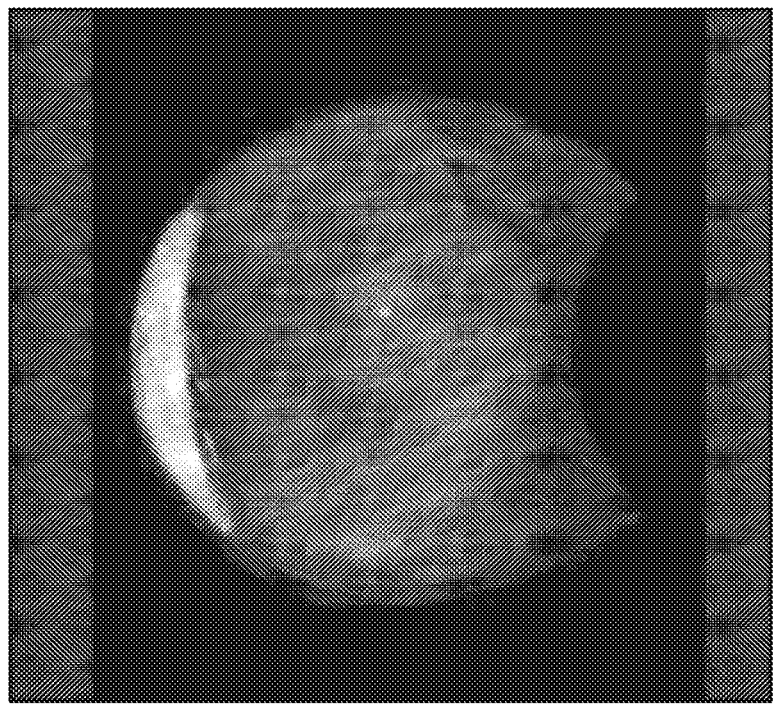
FIG. 14C

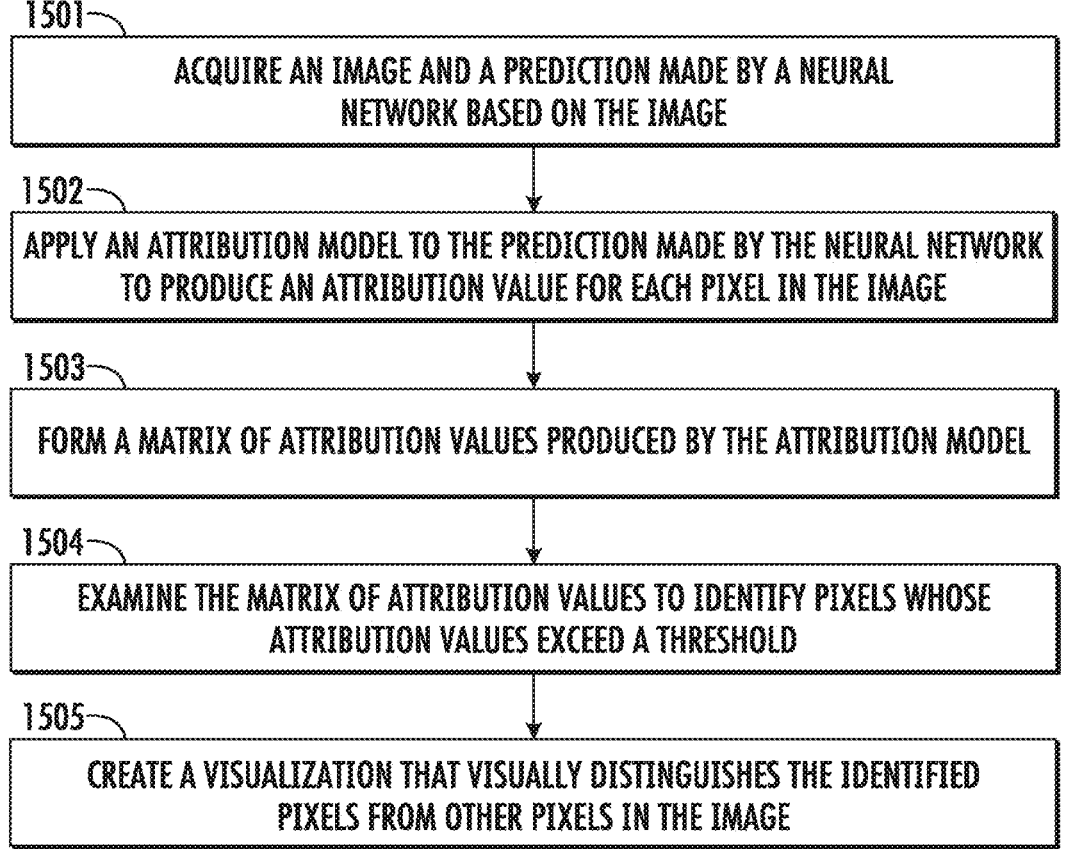

1500

1501 — ACQUIRE AN IMAGE AND A PREDICTION MADE BY A NEURAL NETWORK BASED ON THE IMAGE

1502 — APPLY AN ATTRIBUTION MODEL TO THE PREDICTION MADE BY THE NEURAL NETWORK TO PRODUCE AN ATTRIBUTION VALUE FOR EACH PIXEL IN THE IMAGE

1503 — FORM A MATRIX OF ATTRIBUTION VALUES PRODUCED BY THE ATTRIBUTION MODEL

1504 — EXAMINE THE MATRIX OF ATTRIBUTION VALUES TO IDENTIFY PIXELS WHOSE ATTRIBUTION VALUES EXCEED A THRESHOLD

1505 — CREATE A VISUALIZATION THAT VISUALLY DISTINGUISHES THE IDENTIFIED PIXELS FROM OTHER PIXELS IN THE IMAGE

FIG. 15

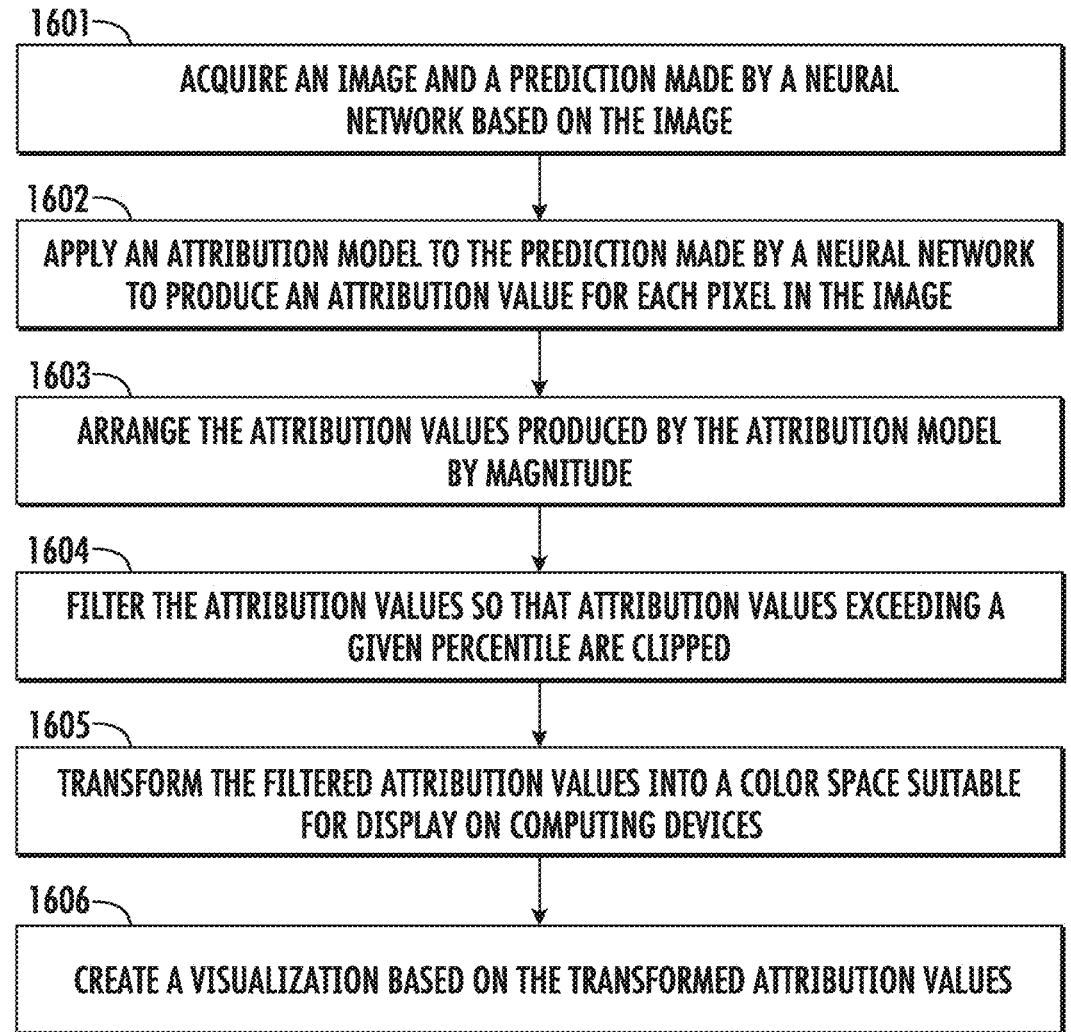

1600

1601 ─ ACQUIRE AN IMAGE AND A PREDICTION MADE BY A NEURAL NETWORK BASED ON THE IMAGE

1602 ─ APPLY AN ATTRIBUTION MODEL TO THE PREDICTION MADE BY A NEURAL NETWORK TO PRODUCE AN ATTRIBUTION VALUE FOR EACH PIXEL IN THE IMAGE

1603 ─ ARRANGE THE ATTRIBUTION VALUES PRODUCED BY THE ATTRIBUTION MODEL BY MAGNITUDE

1604 ─ FILTER THE ATTRIBUTION VALUES SO THAT ATTRIBUTION VALUES EXCEEDING A GIVEN PERCENTILE ARE CLIPPED

1605 ─ TRANSFORM THE FILTERED ATTRIBUTION VALUES INTO A COLOR SPACE SUITABLE FOR DISPLAY ON COMPUTING DEVICES

1606 ─ CREATE A VISUALIZATION BASED ON THE TRANSFORMED ATTRIBUTION VALUES

FIG. 16

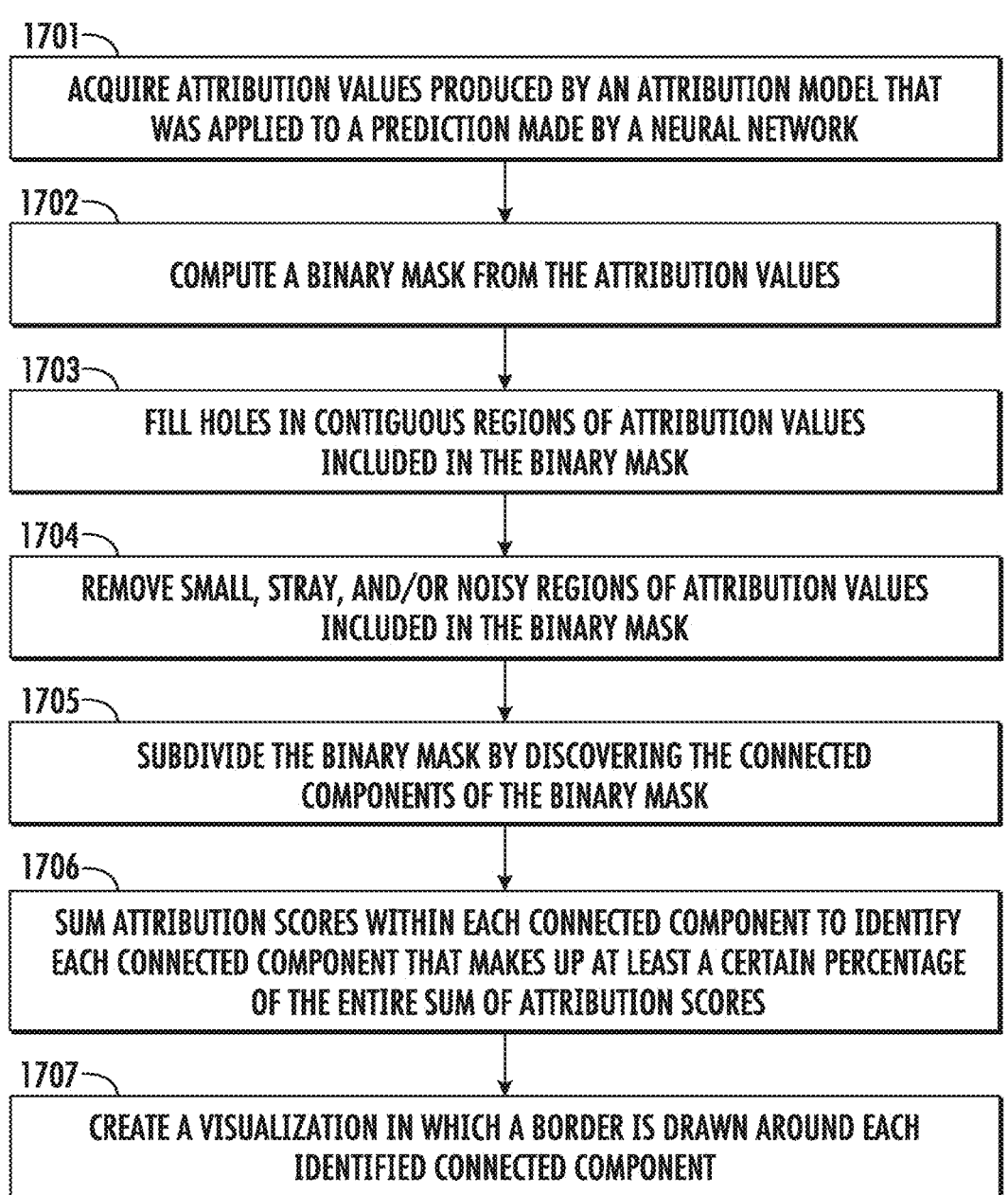

1700

1701 — ACQUIRE ATTRIBUTION VALUES PRODUCED BY AN ATTRIBUTION MODEL THAT WAS APPLIED TO A PREDICTION MADE BY A NEURAL NETWORK

1702 — COMPUTE A BINARY MASK FROM THE ATTRIBUTION VALUES

1703 — FILL HOLES IN CONTIGUOUS REGIONS OF ATTRIBUTION VALUES INCLUDED IN THE BINARY MASK

1704 — REMOVE SMALL, STRAY, AND/OR NOISY REGIONS OF ATTRIBUTION VALUES INCLUDED IN THE BINARY MASK

1705 — SUBDIVIDE THE BINARY MASK BY DISCOVERING THE CONNECTED COMPONENTS OF THE BINARY MASK

1706 — SUM ATTRIBUTION SCORES WITHIN EACH CONNECTED COMPONENT TO IDENTIFY EACH CONNECTED COMPONENT THAT MAKES UP AT LEAST A CERTAIN PERCENTAGE OF THE ENTIRE SUM OF ATTRIBUTION SCORES

1707 — CREATE A VISUALIZATION IN WHICH A BORDER IS DRAWN AROUND EACH IDENTIFIED CONNECTED COMPONENT

FIG. 17

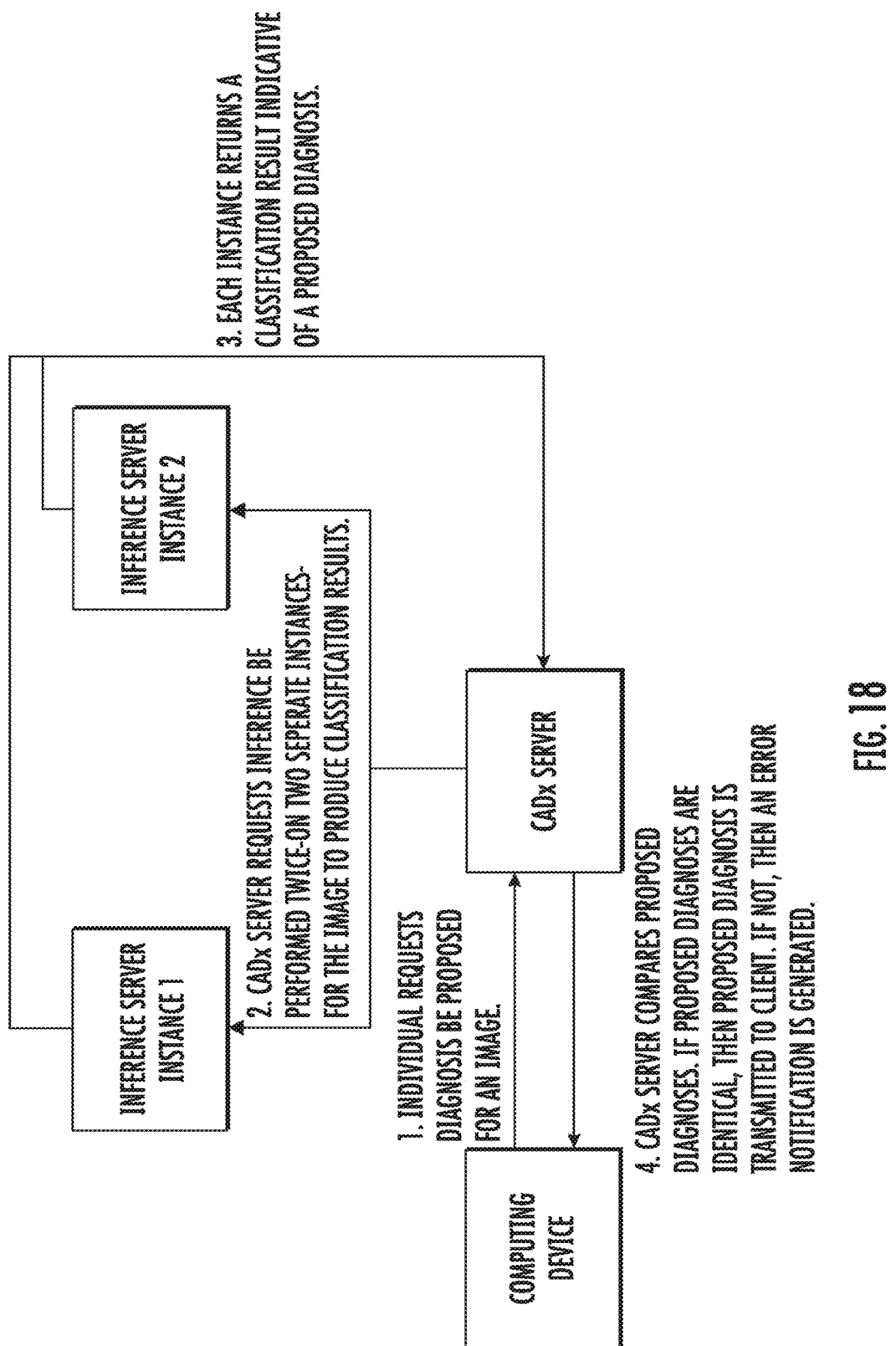

FIG. 18

INFERENCE SERVER INSTANCE 2

INFERENCE SERVER INSTANCE 1

CADx SERVER

COMPUTING DEVICE

1. INDIVIDUAL REQUESTS DIAGNOSIS BE PROPOSED FOR AN IMAGE.

2. CADx SERVER REQUESTS INFERENCE BE PERFORMED TWICE-ON TWO SEPERATE INSTANCES- FOR THE IMAGE TO PRODUCE CLASSIFICATION RESULTS.

3. EACH INSTANCE RETURNS A CLASSIFICATION RESULT INDICATIVE OF A PROPOSED DIAGNOSIS.

4. CADx SERVER COMPARES PROPOSED DIAGNOSES. IF PROPOSED DIAGNOSES ARE IDENTICAL, THEN PROPOSED DIAGNOSIS IS TRANSMITTED TO CLIENT. IF NOT, THEN AN ERROR NOTIFICATION IS GENERATED.

2100

MULTI-VARIABLE HEATMAPS FOR COMPUTER-AIDED DIAGNOSTIC MODELS

PRIORITY CLAIM

This application is based upon and claims the right of priority under 35 U.S.C. § 371 to International Application No. PCT/US2020/058001 filed on Oct. 29, 2020, which claims the benefit of U.S. Provisional Applications 62/927,415, 62/927,426, and 62/927,434 each having a filing date of Oct. 29, 2019. Applicant claims priority to and the benefit of each of such applications and incorporates all such applications herein by reference in its entirety.

TECHNICAL FIELD

Various embodiments concern computer programs and associated computer-implemented techniques for creating visualizations to explain the relationship between the outputs produced by a computer-aided diagnostic (CADx) model and its inputs in a form suitable for human consumption.

BACKGROUND

The process by which visual representations of a human body are captured is referred to as "medical imaging" or "biological imaging." Generally, medical imaging seeks to reveal internal structures hidden by the skin or bones in order to detect the presence of a disease. For example, a series of digital images (or simply "images") corresponding to different aspects of the anatomy of the human body may make it possible to more readily identify abnormalities.

A variety of different technologies may be used to capture these images. Examples of such technologies include x-ray, magnetic resonance imaging (MRI), ultrasonography or ultrasound, endoscopy, microscopy, elastography, tactile imaging, thermography, computed tomography (CT), fluoroscopy, angiography, mammography, positron emission tomography (PET), single photon emission computed tomography (SPECT), and the like. The ever-growing number of images requires that evidence of disease presence be more quickly, accurately, and efficiently identified.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 5A includes an example of a retinal image captured during a diagnostic session.

FIG. 5B shows an example of a visualization that is based on the attributions established by the attribution model.

FIG. 6 depicts a flow diagram of a process for attributing an output produced by a neural network as part of a computer-aided diagnostic process to its input.

FIG. 7 depicts a flow diagram of a process for attributing multiple outputs produced by the multi-headed neural network of a diagnostic model as part of a computer-aided diagnostic process to its input.

FIG. 12 illustrates how morphological transformations can be applied to the attributions produced by an attribution model.

FIG. 13 illustrates an example scenario in which a diagnostic platform applies an attribution model to the prediction generated by a neural network (here, a severity grade for diabetic retinopathy), examines the matrix of attribution values generated by the attribution model to identify the pixels that exceed a specified threshold, and creates a visualization that visually highlights the identified pixels.

FIG. 15 depicts a flow diagram of a process for producing a visualization to explain how a neural network generated a prediction based on an image explain how a neural network generated a prediction based on an image.

FIG. 16 depicts a flow diagram of another process for producing a visualization to explain how a neural network generated a prediction based on an image.

FIG. 17 depicts a flow diagram of a process for outlining clusters of pixels determined to be diagnostically relevant to a prediction made by a neural network.

FIG. 18 illustrates how information may flow between a series of computer servers able to produce predictions indicative of proposed diagnoses.

Figure 1:
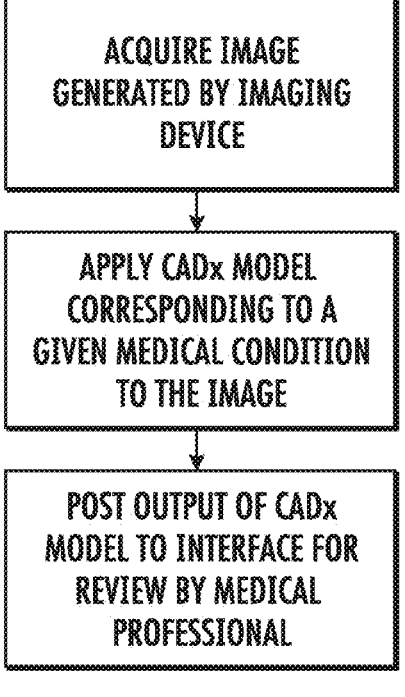
FIG. 1 illustrates an example scenario in which a diagnostic platform acquires a retinal image generated by a fundus camera (also referred to as a "retinal camera"), applies a diagnostic model to the retinal image, and then posts an output produced by the diagnostic model to an interface for review by a medical professional.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Imaging has historically been the most effective means for detecting a variety of ailments. For example, radiological imaging has been shown to be the most effective means for early detection of breast cancer and diabetic retinopathy, among other ailments. However, differentiating the features in an image can be difficult. For instance, the differences between benign and malignant growths may be largely indistinguishable to the human eye.

Accordingly, computer-aided diagnosis technologies have become a part of clinical work in several areas of medicine. To increase the accuracy of image interpretation, a diagnostic platform can apply one or more computer-aided diagnostic (CADx) models (or simply "diagnostic models") to an image. FIG. 1 illustrates an example scenario in which a diagnostic platform acquires a retinal image generated by a fundus camera (also referred to as a "retinal camera"), applies a diagnostic model to the retinal image, and then posts an output produced by the diagnostic model to an interface for review by a medical professional. The output may be a proposed diagnosis with respect to an ailment or a disease (collectively referred to as "medical conditions").

The diagnostic model may be represented by a series of algorithms that are applied, either sequentially or simultaneously, to an image to produce an output that conveys information about a medical condition. The output is normally considered as a "second opinion" by the medical professional responsible for interpreting the image. Thus, diagnostic models can act as decision aids for medical professionals in characterizing the features of an image.

It has become increasingly difficult, however, for medical professionals to discover how an output produced by a diagnostic model can be attributed to its input(s). For instance, a diagnostic platform may apply a diagnostic model represented by an artificial neural network (or simply "neural network") to an input in order to produce an output indicative of a proposed diagnosis for a medical condition. A neural network is a framework of multiple machine learning (ML) algorithms that work together to process complex inputs. Inspired by the biological neural networks that constitute animal brains, neural networks can "learn" to perform tasks by considering examples without being programmed with task-specific rules. For example, a neural network may learn to identify images that include feature(s) indicative of breast cancer by analyzing a series of training images that have been labeled as "breast cancer" or "no breast cancer" and then using the results to identify instances of breast cancer in other images. The neural network can accomplish this without having any prior knowledge about breast cancer. Instead, the neural network can automatically learn features whose presence is indicative of breast cancer from the series of training images.

However, the outputs produced by neural networks can be difficult to interpret. For instance, it is often unclear how a neural network established that an output was appropriate given the input. Simply put, the increasing complexity of diagnostic models has made it difficult to explain their outputs in a comprehensible manner.

Introduced here, therefore, are diagnostic platforms able to attribute the outputs produced by a neural network to its inputs. Neural networks are increasingly being used for critical tasks, such as detecting the presence/progression of medical conditions. Accordingly, the importance of explaining how these neural networks produce outputs has grown in importance. By explaining how outputs are produced by a neural network, a diagnostic platform can build trust with medical professionals responsible for interpreting the outputs, identify possible modes of neural network failure, and identify the latent variable(s) responsible for producing a given output.

Embodiments may be described with reference to particular medical conditions, imaging devices, computer programs, networks, etc. However, those skilled in the art will recognize that these features are similarly applicable to other medical conditions, imaging device types, computer program types, network types, etc. For example, although embodiments may be described in the context of neural networks designed to be applied to retinal images, the relevant features may be similarly applicable to neural networks designed to be applied to images of other parts of the human body.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for acquiring an image generated during a diagnostic session, applying a neural network to the image to produce an output indicative of a proposed diagnosis, determining a contribution of each pixel in the image to the output, producing a visualization that visually highlights at least some of the pixels determined to have contributed to the production of the output, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

Figure 2:
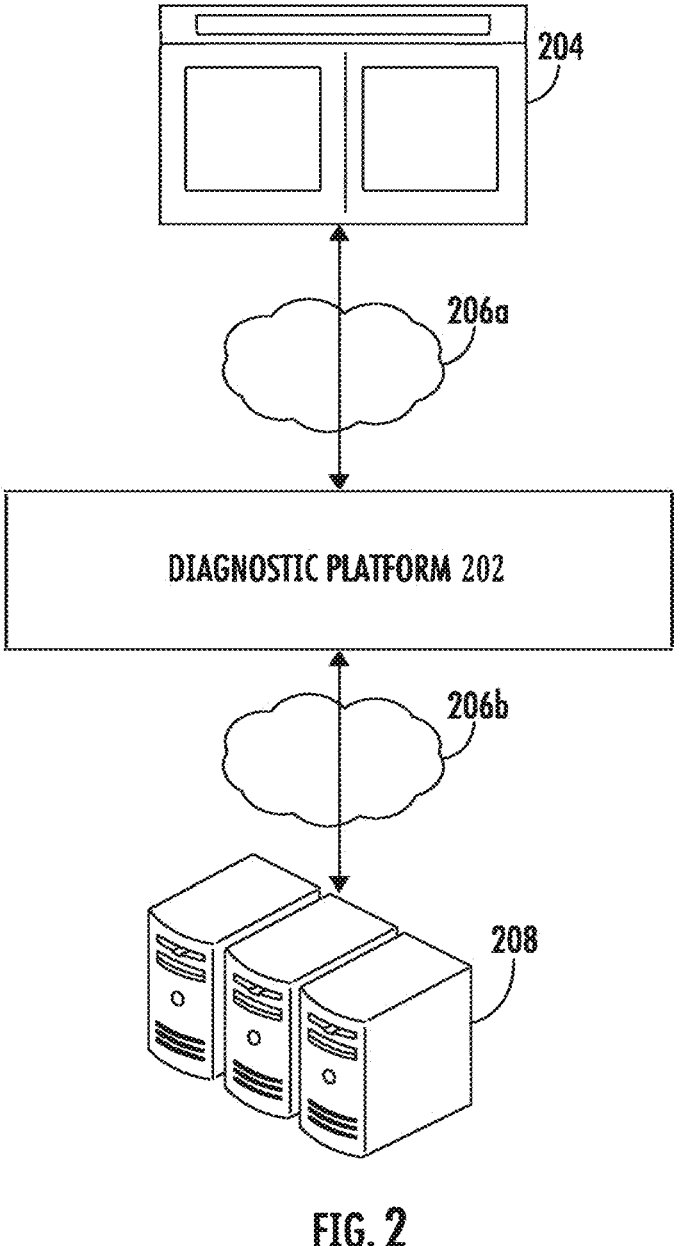
FIG. 2 illustrates a network environment that includes a diagnostic platform able to apply diagnostic models to images captured during diagnostic sessions.

FIG. 2 illustrates a network environment 200 that includes a diagnostic platform 202 able to apply diagnostic models to images captured during diagnostic sessions. One example of a diagnostic model is a neural network model that applies a series of ML algorithms (also referred to as a "neural network") to the pixel data of an image to produce an output. Individuals can interact with the diagnostic platform 202 via an interface 204. For example, medical professionals may access the interface 204 to review outputs produced by diagnostic models. The diagnostic platform 202 may be responsible for applying diagnostic models to images taken of subjects (also referred to as "patients") to identify the diagnostically-relevant segment(s), generate records of the outputs produced by the diagnostic models, etc.

When applied to an image, a diagnostic model may produce an output indicative of the health state of the corresponding subject. The term "health state" can refer to the physical health of the subject with respect to a given medical condition. For example, some diagnostic models are designed to identify features known to be indicative of diabetic retinopathy, while other diagnostic models are designed to identify features known to be indicative of breast cancer.

As shown in FIG. 2, the diagnostic platform 202 may reside in a network environment 200. Thus, the diagnostic platform 202 may be connected to one or more networks 206a-b. The network(s) 206a-b can include personal area networks (PANs), local area networks (LANs), wide area networks (WANs), metropolitan area networks (MANs), cellular networks, the Internet, etc. Additionally or alternatively, the diagnostic platform 202 can be communicatively coupled to computing device(s) over a short-range communication protocol, such as Bluetooth® or Near Field Communication (NFC).

The interface 204 is preferably accessible via a web browser, desktop application, mobile application, or over-the-top (OTT) application. Accordingly, the interface 204 may be viewed on a desktop computer, tablet computer, mobile workstation, mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diagnostic platform 202 are hosted locally. That is, the diagnostic platform 202 may reside on the computing device used to access the interface 204. For example, the diagnostic platform 202 may be embodied as a mobile application executing on a mobile phone or a desktop application executing on a mobile workstation. Other embodiments of the diagnostic platform 202 are executed by a cloud computing service operated by Amazon Web Services® (AWS), Google Cloud Platform™, Microsoft Azure®, or a similar technology. In such embodiments, the diagnostic platform 202 may reside on a host computer server that is communicatively coupled to one or more content computer servers 208. The content computer server(s) 208 can include images to be examined for the purpose of rendering diagnoses, subject information (e.g., age, sex, health diagnoses, etc.), imaging device information (e.g., resolution, expected file size, etc.), diagnostic models, and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause the necessary assets (e.g., images, diagnostic models, or processing operations) to be downloaded at a single point in time or on a periodic basis (e.g., weekly, daily, or hourly).

Figure 3:
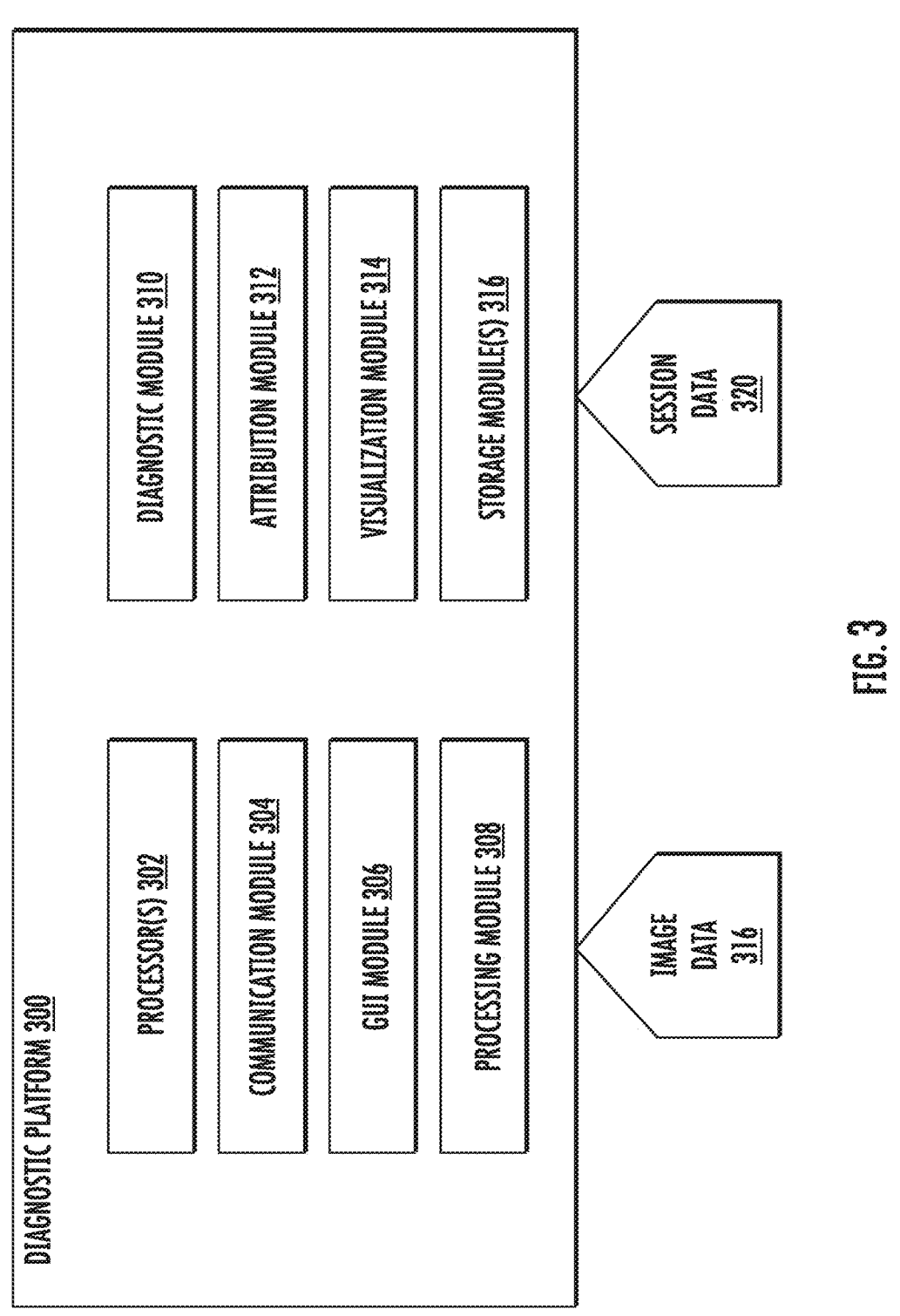
FIG. 3 depicts the high-level architecture of a diagnostic platform able to discover how the outputs produced by a diagnostic model can be attributed to its input

FIG. 3 depicts the high-level architecture of a diagnostic platform 300 able to discover how the outputs produced by a diagnostic model can be attributed to its input(s). Such action enables the diagnostic platform 300 to explain how the outputs are produced by the diagnostic model. For instance, the diagnostic platform 300 may acquire an image and then apply a diagnostic model (e.g., a neural network model) to the image to produce an output that conveys information about a medical condition. Thereafter, the diagnostic platform 300 may produce a visualization that visually highlights the pixels considered as evidence of the medical condition by the diagnostic model.

The diagnostic platform 300 can include one or more processors 302, a communication module 304, a graphical user interface (GUI) module 306, a processing module 308, a diagnostic module 310, an attribution module 312, a visualization module 314, and one or more storage modules 316. In some embodiments a single storage module includes multiple computer programs for performing different operations (e.g., metadata extraction, image processing, feature analysis), while in other embodiments each computer program is hosted within a separate storage module. Embodiments of the diagnostic platform 300 may include some or all of these components, as well as other components not shown here.

The processor(s) 302 can execute modules from instructions stored in the storage module(s) 316, which can be any device or mechanism capable of storing information. For example, the processor(s) 302 may execute the GUI module 306, processing module 308, diagnostic module 310, attribution module 312, or visualization module 314.

The communication module 304 can manage communications between various components of the diagnostic platform 300. The communication module 304 can also manage communications between the computing device on which the diagnostic platform 300 resides and another computing device.

For example, the diagnostic platform 300 may reside on a mobile workstation in the form of a desktop application. In such embodiments, the communication module 304 can facilitate communication with a network-accessible computer server responsible for supporting the desktop application and/or an imaging device responsible for generating images of subjects. The communication module 304 may facilitate communication with various data sources through the use of application programming interfaces (APIs), bulk data interfaces, etc. Examples of data sources include network-accessible databases, other desktop applications residing on the mobile workstation, etc.

As another example, the diagnostic platform 300 may reside on a server system that includes one or more network-accessible computer servers. In such embodiments, the communication module 304 can communicate with a computer program executing on a computing device accessible to an individual, such as a mobile phone, desktop computer, or mobile workstation. For example, a medical professional may review visualizations produced by the visualization module 314 by interacting with the diagnostic platform 300 via a web browser. As another example, the medical professional may review outputs produced by the diagnostic module 310 via the web browser. Those skilled in the art will recognize that the components of the diagnostic platform 300 can be distributed between the server system and the computing device in various manners. For example, some data (e.g., images of subjects) may reside on the computing device for privacy purposes, while other data (e.g., diagnostic models programmed for producing outputs indicative of proposed diagnoses, attribution models programmed for producing attributions measures, and subject profiles) may reside on the server system.

The GUI module 306 can generate the interface(s) through which an individual can interact with the diagnostic platform 300. For example, an interface may include a proposed diagnosis generated by a diagnostic model applied by the diagnostic module 310 and a visualization generated by the visualization module 314. As further described below, the visualization may serve as an explanation for how the diagnostic model established the proposed diagnosis was an appropriate output. As another example, an interface may include information regarding the subject involved in a diagnostic session.

The processing module 308 can apply operation(s) to image data 318 and/or session data 320 acquired by the diagnostic platform 300. In some embodiments, the image data 318 and session data 320 are acquired from the same source. For example, the diagnostic platform 300 may be configured to acquire Digital Imaging and Communications in Medicine (DICOM) data objects, each of which includes image data 318 corresponding to an image generated during a diagnostic session and session data 320 specifying an attribute of the imaging device responsible for capturing the image, the subject captured in the image, or the diagnostic session itself. In such embodiments, upon receiving a DICOM data object, the processing module 308 may parse the session data 320 to discover an attribute related to the imaging device, subject, or diagnostic session. This attribute may be used by the diagnostic module 310 to identify an appropriate diagnostic model. For example, if the processing module 308 discovers that the image under consideration was generated by a retinal camera, then the diagnostic module 310 may identify a diagnostic model corresponding to a medical condition that affects the eye.

In other embodiments, the image data 318 and the session data 320 are acquired from different sources. For example, the diagnostic platform 300 may be configured to acquire session data 320 from a network-accessible storage medium. The session data 320 may be representative of information provided by an individual as part of a diagnostic session. The individual may be the subject (who may have provided the information as part of an intake procedure) or a medical professional (who may have provided the information over the course of the diagnostic session). In such embodiments, if the image data 318 is acquired in the form of a DICOM data object, then the session data 320 may be acquired from multiple sources (e.g., the DICOM data object and the network-accessible storage medium), though different information may be derived from the session data 320 acquired from each source. Alternatively, the image data 318 may be acquired in the form of images in the Joint Photographic Experts Group (JPEG) format, Tagged Image File Format (TIFF), Portable Network Graphics (PNG) format, etc.

Examples of sources include the computing device on which the diagnostic platform 300 resides, an imaging device to which the computing device is connected, and a network-accessible storage medium to which the computing device is connected. Different types of images may be acquired by the diagnostic platform 300 from multiple sources (e.g., different imaging devices). For example, the diagnostic platform 300 could acquire two-dimensional (2D) images, three-dimensional (3D) images, colored images, grayscale images (e.g., those captured during a fluorescein angiography procedure), etc. The processing module 308 may be responsible for applying operation(s) to ensure that image data 318 received from multiple sources is in a compatible format that can be processed by the other modules. In some embodiments, the processing module 308 is able to convert colored images into grayscale images, or vice versa.

A source may be configured to continuously or periodically transmit image data 318 and/or session data 320 to the diagnostic platform 300. In some embodiments, the source continually uploads data to the diagnostic platform 300 so long as the source remains communicatively coupled to the computing device on which the diagnostic platform 300 resides (e.g., via a Bluetooth® communication channel). For example, image data 318 may be streamed from the source to the diagnostic platform 300 in real time as images are generated. In other embodiments, the source uploads data to the diagnostic platform 300 on a periodic basis (e.g., hourly, daily, or weekly). For example, session data 320 representative of information provided by an individual (e.g., a medical professional) over the course of several diagnostic sessions may be delivered in a single batch to the diagnostic platform 300. In such embodiments, the processing module 308 may parse the session data 320 to identify the information corresponding to the subject in each image represented by the image data 318. The diagnostic platform 300 can be configured to pull image data 318 and/or session data 320 from the source. Additionally or alternatively, the source can be configured to push image data 318 and/or session data 320 to the diagnostic platform 300. In some embodiments, an individual (e.g., an administrator or a medical professional) is able to configure these push/pull settings. These settings can be configured on a source-by-source basis.

After acquiring image data 318, the diagnostic module 310 can identify an appropriate diagnostic model to apply to the image. For example, the diagnostic module 310 may identify the appropriate diagnostic model based on an attribute derived from session data 320 corresponding to the image data 318. Generally, the diagnostic model is one of multiple diagnostic models maintained in a library stored in the storage module(s) 314, and each diagnostic model may be associated with a different medical condition. The diagnostic model can include algorithm(s) that, when applied to the image data 318, produce an output that conveys information about a medical condition. For example, if the image data 318 is representative of a retinal image, then the output produced by the diagnostic model may be indicative of a proposed diagnosis for an eye-related medical condition such as diabetes, age-macular degeneration (AMD), glaucoma, neoplasm, diabetic retinopathy, etc. The output is normally considered as a "second opinion" by the medical professional responsible for interpreting the retinal image. Thus, a diagnostic model can act as a decision aid for the medical professional in characterizing the diagnostically-relevant features of the retinal image.

However, it has become increasingly difficult for medical professionals to discover how an output produced by a diagnostic model can be attributed to its input(s). This is especially true for certain kinds of diagnostic models, such as neural network models. As further described below, the attribution module 312 can apply an attribution model to an output produced by a diagnostic model applied by the diagnostic module 310 to produce attribution values (also referred to as "attribution measures"). Each attribution value is indicative of the importance of the corresponding pixel to the output.

The visualization module 314, meanwhile, can create visualizations based on the attribution values produced by the attribution module 312. The visualizations may be designed based on the input considered by the diagnostic model applied by the diagnostic module 310. For example, if the diagnostic module 310 provides an image to the diagnostic model as input, then the visualization module 314 may produce a heatmap designed to overlay the image. A "heatmap" is a visual representation of data that uses color-coding to represent different values. Thus, the visualization module 314 may produce a heatmap that visually highlights the pixels determined to have contributed to the output produced by the diagnostic model. As further described below, these pixels will generally have high attribution values as determined by the attribution module 312.

Figure 4:
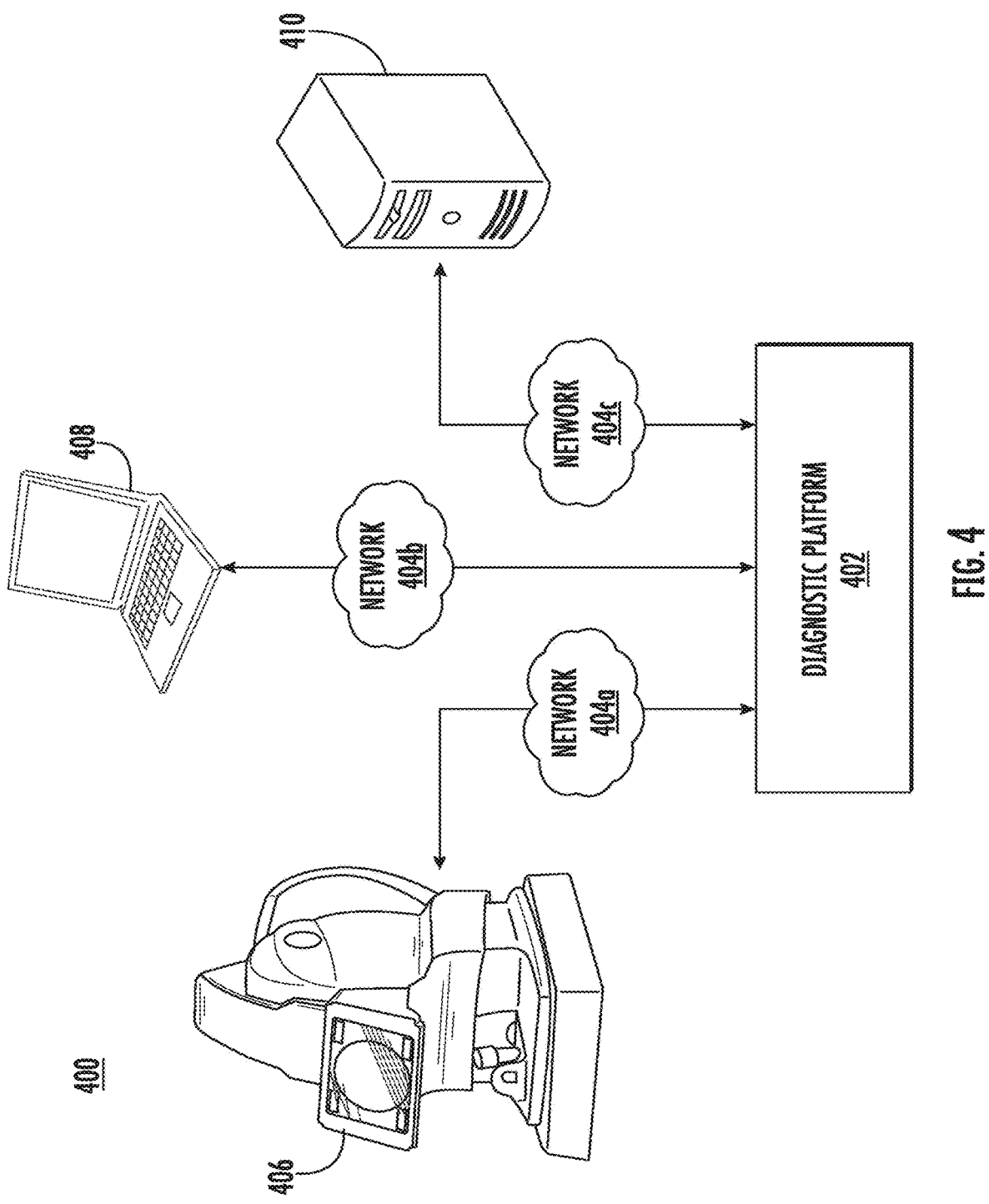
FIG. 4 depicts an example of a communication environment that includes a diagnostic platform configured to acquire data from one or more sources.

FIG. 4 depicts an example of a communication environment 400 that includes a diagnostic platform 402 configured to acquire data from one or more sources. Here, for example, the diagnostic platform 402 receives data from a retinal camera 406, laptop computer 408, and network-accessible server system 410 (collectively referred to as the "networked devices"). The data may include pixel data and/or session data.

The networked devices can be connected to the diagnostic platform 402 via one or more computer networks 404a-c. The computer network(s) 404a-c can include PANs, LANs, WANs, MANs, cellular networks, the Internet, etc. Additionally or alternatively, the networked devices may communicate with one another over a short-range communication protocol, such as Bluetooth® or Near Field Communication (NFC). For example, the diagnostic platform 402 resides on the network-accessible server system 410 in some embodiments. In such embodiments, data received from the network-accessible server system 410 need not traverse any computer networks. However, the network-accessible server system 410 may be connected to the retinal camera 406 and the laptop computer 408 via separate Wi-Fi communication channels.

Embodiments of the communication environment 400 may include some or all of the networked devices. For example, some embodiments of the communication environment 400 include a diagnostic platform 402 that receives image data from the retinal camera 406 and session data from the network-accessible server system 410 on which it resides. As another example, some embodiments of the communication environment 400 include a diagnostic platform 402 that receives image data from a variety of different retinal cameras located in different environments (e.g., different clinics).

While the communication environment 400 of FIG. 4 includes a retinal camera 406, those skilled in the art will recognize that the diagnostic platform 402 can be designed to process images generated by other imaging devices. Examples of imaging devices include retinal cameras, x-ray generators and detectors, MRI machines, CT machines, digital cameras (e.g., digital single-lens reflex (DSLR) cameras and mirrorless cameras), etc.

Attribution Methodologies for Neural Networks

A diagnostic platform can apply a diagnostic model to an image captured during a diagnostic session to produce an output indicative of a proposed diagnosis for a medical condition. One example of a diagnostic model is a neural network model that applies a neural network to the pixel data of an image to produce an output. The outputs produced by neural networks, however, can be difficult to interpret.

For instance, it can be unclear how a neural network, especially a deep neural network with multiple layers between the input and output layers, establishes that an output was appropriate given the input. Introduced here are diagnostic platforms able to properly attribute the outputs produced by a neural network to its inputs. Some neural networks are designed to produce a single output (e.g., a proposed diagnosis for a medical condition) based on a single input (e.g., an image), while some neural networks are designed to produce multiple outputs (e.g., proposed diagnoses for multiple medical conditions) based on a single input (e.g., an image). These neural networks can be referred to as "single-headed neural networks" and "multi-headed neural networks," respectively. While features may be described in the context of single-headed neural networks for simplicity, the features are equally applicable to multi-headed neural networks unless otherwise noted.

A neural network may be designed to produce an output (also referred to as a "prediction") based on the features discovered within an input. One approach to explaining the output produced by a neural network is to attribute the prediction back to features of the input (e.g., the pixels if the input is an image). The attribution problem can be summarized as follows: Given input $x = (x_1, x_2, \ldots, x_n) \in \mathbb{R}$ and function $F: \mathbb{R}^n \to [0, 1]$ that represents a neural network, how can a diagnostic platform attribute the output to the input on a per-element basis?

An example of a potential solution to the attribution problem is the attribution method called "Integrated Gradients" is provided by Sundararajan et al. in "Axiomatic Attribution for Deep Networks," arXiv:1703.01365 [cs.LG]. The intent behind the development of Integrated Gradients was to understand the input-output behavior of a deep network such as a neural network. Attributions can be useful in a variety of contexts. For instance, Integrated Gradients can be employed by a product driven by machine learning, such as the diagnostic platforms described herein, to provide a rationale for the outputs produced by the product.

Designing an attribution model representative of an attribution method can be difficult because its success is difficult to evaluate empirically. For instance, it can be difficult to tease apart errors that stem from misbehavior of the attribution model versus misbehavior of the attribution method itself. Conventional attribution methods are generally unsuitable for neural networks because they do not satisfy two axioms, sensitivity and implementation invariance. An attribution method will satisfy the sensitivity axiom if for every input and baseline that differ in one feature but have different predictions, the differing feature is given a non-zero attribution. An attribution method will satisfy the implementation invariance axiom if the attributions are always identical for two functionally-equivalent neural networks.

As noted above, conventional attribution methods fail to satisfy these two axioms. For example, approaches based on gradients, deconvolution, layer-wise relevance propagation (LRP), and back-propagation violate the sensitivity axiom when applied to neural networks, while approaches based on LRP and back-propagation violate the implementation invariance axiom when applied to neural networks.

Integrated Gradients combines the implementation invariance of a gradients-based approach with the sensitivity of an LRP-based approach. Given a function $F: \mathbb{R}^n \rightarrow [0, 1]$ that represents a neural network, let $x \in \mathbb{R}^n$ be the input image and $x' \in \mathbb{R}^n$ be the baseline image (also referred to as the "reference image"). The baseline image may be an image comprised entirely of black pixels. Black reference images tend to overemphasize bright features in the input image.

An attribution model (referred to as an "Integrated Gradients model") can consider the straight-line path (in $\mathbb{R}^n$) from the baseline image (x') to the input image (x) and then compute the gradients at all points along the straight-line path. The attribution model can then obtain integrated gradients by cumulating these gradients. The integrated gradients are defined as the path integral of the gradients along the straight-line path from the baseline image (x') to the input image (x). The integrated gradient along the $i^{th}$ dimension for an input image (x) and baseline image (x') is shown in Equation 1. Here, $$\frac{\partial F(x)}{\partial x_i}$$

is the gradient of F(x) along the $i^{th}$ dimension.

$$IntegratedGrads_i(x) := (x_i - x_i') \times \int_{a=0}^{1} \frac{\partial F(x' + a \times (x - x'))}{\partial x_i} \quad \text{(Eq. 1)}$$

While the attribution model will aggregate the gradients along the straight-line path between the baseline image (x') and the input image (x), there are many other non-straight-line paths that can be followed between the baseline image (x') and the input image (x). Each path will yield a different attribution method (and thus a different attribution model).

Before the attribution model is applied to an output produced by a neural network, a baseline image must be selected. Generally, the individual responsible for implementing the attribution model will select the baseline image, though a diagnostic platform could automatically select the baseline image on behalf of the individual. As noted above, the baseline image may be an image comprised entirely of black pixels. The individual may pick from possible baseline images based on the intended application. For example, because the black image signifies the absence of objects, selecting the black image as the baseline image may result in clearer visualizations of edge features.

The integral of integrated gradients can be efficiently approximated by the attribution model via a summation. In particular, the attribution model can sum the gradients at the points occurring at sufficiently small intervals along the straight-line path from the baseline image (x') to the input image (x), as shown in Equation 2.

$$\text{(Eq. 2)}$$

$$IntegratedGrads_i^{approx}(x) :=$$

$$(x_i - x_i') \times \sum_{k=1}^{m} \frac{\partial F\left(x' + \frac{k}{m} \times (x - x')\right)}{\partial x_i} \times \frac{1}{m}$$

Here, m is the number of steps in the approximation of the integral. Because the integral has been approximated via a summation, the attribution model can compute the gradient using a for loop that makes repeated calls to a gradient operator. A "for loop" is a control flow statement in programming for specifying iteration, which allows code to be executed repeatedly. Generally, the attribution model approximates the integral using 20 to 300 steps. As the number of steps increases, the time required to compute the integral increases while the error percentage decreases. Accordingly, the integral may be approximated using the minimum number of steps needed to achieve less than a predetermined error percentage (e.g., 3% or 5%).

Diabetic retinopathy is a complication of diabetes caused by damage to the blood vessels in the retina. To detect the presence/progression of diabetic retinopathy in an individual (also referred to as a "subject" or "patient"), an image of the retina may be captured during a diagnostic session. FIG. 5A includes an example of a retinal image captured during a diagnostic session.

As noted above, a diagnostic platform may apply a neural network model to the image to produce an output indicative of a proposed diagnosis. Here, for example, the diagnostic platform has applied a neural network model whose output indicated that the individual is likely suffering from severe non-proliferative diabetic retinopathy. To study the importance of features in the image on the output produced by the neural network, the diagnostic platform can apply the attribution model described above. Additional insight into the relationship between the output (e.g., the proposed diagnosis) and the input (e.g., the retinal image) may be useful for building trust in the neural network, making predictions for borderline cases, and obtaining insights for further testing, screening, etc.

FIG. 5B shows an example of a visualization that is based on the attributions established by the attribution model. As shown in FIG. 5B, the visualization can overlay a version of the input image (here, a grayscale version of the input image) to make the explanation more readily comprehensible. After applying the attribution model, the diagnostic platform can aggregate the integrated gradients along a color channel and then overlay the aggregated integrated gradients on the input image or a version of the input image.

As further described below, pixels with positive attributions can be shown along one color channel while pixels with negative attribution can be shown along another color channel. Thus, a medical professional may be able to simultaneously examine positive and negative attributions. Said another way, the medical professional can examine the feature(s) supporting the output produced by the diagnostic model and the feature(s) opposing the output produced by the diagnostic model. In FIG. 5B, the integrated gradients are localized to pixels that appear to correspond to damaged blood vessels in the retina.

FIG. 6 depicts a flow diagram of a process 600 for attributing an output produced by a neural network as part of a computer-aided diagnostic process to its input. By establishing the relationship between the output and input, a diagnostic platform can improve confidence in the outputs produced by the neural network. Such action may be critical if the diagnostic platform is responsible for performing sensitive tasks such as rendering proposed diagnoses.

Initially, a diagnostic platform can acquire an image generated during a diagnostic session (step 601). In some embodiments the diagnostic platform acquires the image directly from the imaging device responsible for generating the image, while in other embodiments the diagnostic platform acquires the image from some other source. For example, the diagnostic platform may acquire the image from a network-accessible storage medium managed by clinic, hospital, etc. In some embodiments, the diagnostic platform processes the image by removing artifacts, varying the coloration, cropping pixels, etc.

The diagnostic platform can then select a diagnostic model from a library of diagnostic models based on a characteristic of the image (step 602). In some embodiments, the characteristic is derived from the image itself. For example, the diagnostic platform may discover that the image is a retinal image upon examining its pixel data. In other embodiments, the characteristic is derived from session data that accompanies the image. For example, the diagnostic platform may infer that the image is a retinal image by examining metadata created by the imaging device responsible for generating the image. The metadata may specify the image is related to the left eye or right eye, the model of retinal camera, etc. Thus, the diagnostic platform may establish that the image is a retinal image despite metadata not explicitly specifying as much.

The diagnostic platform may automatically select the diagnostic model based on which part(s) of the human body have been captured in the image. For example, upon determining that the image is a retinal image, the diagnostic platform may select a diagnostic model associated with at least one ocular condition. Alternatively, the diagnostic platform may select the diagnostic model based on input indicative of a selection of a medical condition. For example, a medical professional responsible for examining the image may request that the diagnostic platform apply a diagnostic model associated with a particular ocular condition.

The diagnostic platform can then apply the diagnostic model to the image to produce an output indicative of a proposed diagnosis (step 603). As noted above, the diagnostic model may be represented as a neural network that produces at least one output based on a single input. In some embodiments, the neural network is designed to produce a binary output that specifies whether the individual captured in the image is affected by a given medical condition. In other embodiments, the neural network is designed to produce a non-binary output that specifies a severity grade of a given medical condition. For example, a neural network may predict the severity grade of diabetic retinopathy by examining retinal images may produce outputs such as no diabetic retinopathy, mild diabetic retinopathy, moderate diabetic retinopathy, and severe diabetic retinopathy.

Thereafter, the diagnostic platform can determine the contribution of each pixel in the image to the output (step 604). For example, the diagnostic platform may apply an attribution model to produce an attribution of the output on a per-pixel basis. In particular, the attribution model may be programmed to identify a baseline image and then estimate the contribution of each pixel in the image to the output based on a comparison to a corresponding pixel of the baseline image. The reference image may be an image comprised entirely of black pixels. Formally, assuming the neural network is represented by a function $F: \mathbb{R}^n \rightarrow [0, 1]$ and the input $x=(x_1, \ldots, x_n) \in \mathbb{R}^n$ then the attribution of the prediction at input x relative to a baseline input x' is a vector $A_F(x, x')=(a_1, \ldots, a_n) \in \mathbb{R}n$, where $a_i$ is the contribution of $x_i$ to the prediction $F(x)$. When the attribution model is applied to the output (e.g., the proposed diagnosis) and input (e.g., the image), the attribution model may produce a matrix of attribution values having the same dimensions as the image. For example, the attribution model may create a 1024×1024 matrix with a separate entry for each pixel in a 1024×1024 image.

Then, the diagnostic platform can identify the pixels that contributed to the production of the output (step 605). For example, the attribution model may identify all pixels corresponding to attribution values exceeding a specified threshold. By filtering the attribution values produced by the attribution model, the diagnostic platform can identify the pixels determined to have a diagnostically-relevant impact on the output. The diagnostic platform will normally discover that multiple adjacent pixels (also referred to as a "cluster of pixels") have contributed to the output in a similar manner. In some embodiments, the diagnostic platform may filter the pixels by attribution value to remove all clusters of pixels having less than a predetermined number of pixels (e.g., one, three, five, or ten pixels). In some instances, the diagnostic platform will identify multiple non-contiguous clusters of pixels throughout the image. In FIG. 5B, for example, the diagnostic platform has identified multiple clusters of pixels in the lower-left and upper-right quadrants of the retinal image. These clusters of pixels may correspond to different features (e.g., different lesions or microaneurysms).

The diagnostic platform may cause display of a visualization that causes the pixel(s) determined to have contributed to the output to be visually distinguishable from the other pixels in the image (step 606). For example, the diagnostic platform may cause each cluster of pixels to be outlined. As another example, the diagnostic platform may clip a cluster of pixels from the image and then cause display of the clipped cluster of pixels. As further described below, there are a variety of ways in which the diagnostic platform can draw the attention of an individual to the pixels determined to have contributed to the output.

FIG. 7 depicts a flow diagram of a process 700 for attributing multiple outputs produced by the multi-headed neural network of a diagnostic model as part of a computer-aided diagnostic process to its input. As noted above, a "multi-headed neural network" is designed to produce multiple outputs based on a single input.

Steps 701-705 of FIG. 7 are similar to steps 601-605 of FIG. 6. By applying a multi-headed neural network, however, the diagnostic platform will produce multiple outputs indicative of multiple proposed diagnoses (e.g., for different medical conditions). For example, if the image is a retinal image, then a multi-headed neural network may produce separate diagnoses for diabetes, AMD, glaucoma, neoplasm, diabetic retinopathy, or another eye-related medical condition.

The diagnostic platform can determine, for each output of the multiple outputs, the contribution of each pixel in the image to the corresponding output (step 704). For example, the diagnostic platform may apply an attribution model to produce an attribution of each output on a per-pixel basis. If the diagnostic model applied to the image is represented as a multi-headed neural network, then the diagnostic platform may apply the attribution model per head to identify the pixels that contributed to the production of each output (step 705). As noted above, the diagnostic platform will normally discover that one or more clusters of pixels have contributed to each output. In some embodiments, the diagnostic platform may filter the pixels by attribution value to remove all clusters of pixels having less than a predetermined number of pixels (e.g., one, three, five, or ten pixels). Accordingly, the diagnostic platform may identify, for each output, one or more clusters of pixels, each of which includes at least the predetermined number of pixels.

As noted above, when the attribution model is applied to a single output (e.g., a proposed diagnosis) and input (e.g., the image), the attribution model will produce a matrix of attribution values having the same dimensions as the image. If the attribution model is applied to multiple outputs produced by a multi-headed neural network, then the attribution model will produce a separate matrix of attribution values for each output of the multiple outputs. Thus, each pixel in the image may be associated with a vector of attribution values, and each attribution value included in the vector may correspond to a different output.

Those skilled in the art will recognize that a given pixel could be included in multiple clusters associated with different medical conditions. For example, if the diagnostic platform identifies a first cluster of pixels associated with a first medical condition and a second cluster of pixels associated with a second medical condition, the first and second clusters of pixels may at least partially overlap one another. That is, the first and second clusters of pixels may share at least one pixel in common.

Thereafter, the diagnostic platform can produce a visualization that visually distinguishes the pixels in the image considered as evidence of each medical condition by the multi-headed neural network (step 706). Then, the diagnostic platform can cause display of the visualization on an electronic device (step 707). The electronic device may be associated with a medical professional responsible for managing the diagnostic session. In some embodiments, the visualization includes a multi-variable heatmap that visually distinguishes the pixels in the image considered as evidence of each medical condition by the multi-headed neural network. In such embodiments, the diagnostic platform may create multiple heatmaps by producing, for each output, a separate heatmap that distinguishes the pixels in the image considered as evidence of the corresponding medical condition by the multi-headed neural network, and then compiling the multiple heatmaps into the multi-variable heatmap. In other embodiments, the visualization component outlines the cluster(s) of pixels corresponding to each output in a visually distinctive manner (e.g., in a different color, stroke type, etc.).

Unless contrary to physical possibility, it is envisioned that the steps described above may be performed in various sequences and combinations. For example, the diagnostic platform may determine the contribution of each pixel in the image to a limited subset of the outputs produced by a multi-headed neural network associated with multiple medical conditions. Such action may be performed if the medical professional specifies an interest in a subset of the multiple medical conditions.

Other steps may also be included in some embodiments. For example, the diagnostic platform may store the visualization and/or the image in a profile associated with an individual captured in the image. This may be useful for medical professionals interested in tracking the presence/progression of a medical condition over time. As another example, the diagnostic platform may receive input indicative of a selection of a particular output of multiple outputs produced by a multi-headed neural network. In such embodiments, the diagnostic platform may produce a single-variable heatmap that visually distinguishes the pixels in the image considered as evidence of the medical condition corresponding to the particular output. Thus, the diagnostic platform may enable individuals (e.g., medical professionals) to interact with the visualizations to better understand the relationships between the output(s) and input of a neural network.

Visualization Methodologies for Explaining Neural Network Attribution

Neural networks can be used for a variety of computer-vision tasks. For example, a neural network may be designed to produce a prediction based on the features discovered within an image. One approach to explaining the prediction of a neural network is to attribute the prediction back to the base features (e.g., the pixels in the image). Several attribution methods have been proposed in the literature. Examples of attribution methods are provided by Baehrens et al. in "How to Explain Individual Classification Decisions," *Journal of Machine Learning Research* (2010); Binder et al. in "Layer-wise Relevance Propagation for Neural Networks with Local Renormalization Layers," *CoRR* (2016); and Lundberg et al. in "A Unified Approach to Interpreting Model Predictions," *Advances in Neural Information Processing Systems* 30 (2017). An attribution method called "Integrated Gradients" is discussed at length above. The resulting attributions can assist an individual (e.g., a medical professional) in interpreting the prediction.

Attribution methods fall into two broad categories. Some attribution methods assign influence proportional to the gradient of the prediction score with respect to the input (i.e., the image). Other attribution methods propagate or redistribute the prediction score, layer by layer of the neural network, from the output back to its input. In all cases, however, the attribution method will assign each pixel a score (also referred to as an "attribution value") proportional to its importance. This score could be positive or negative depending on the polarity of the influence of the pixel on the prediction score. Each attribution method is justified in principled ways, though the justification principles differ across attribution methods since there is no such thing as a universally optimal explanation.

Figure 8:
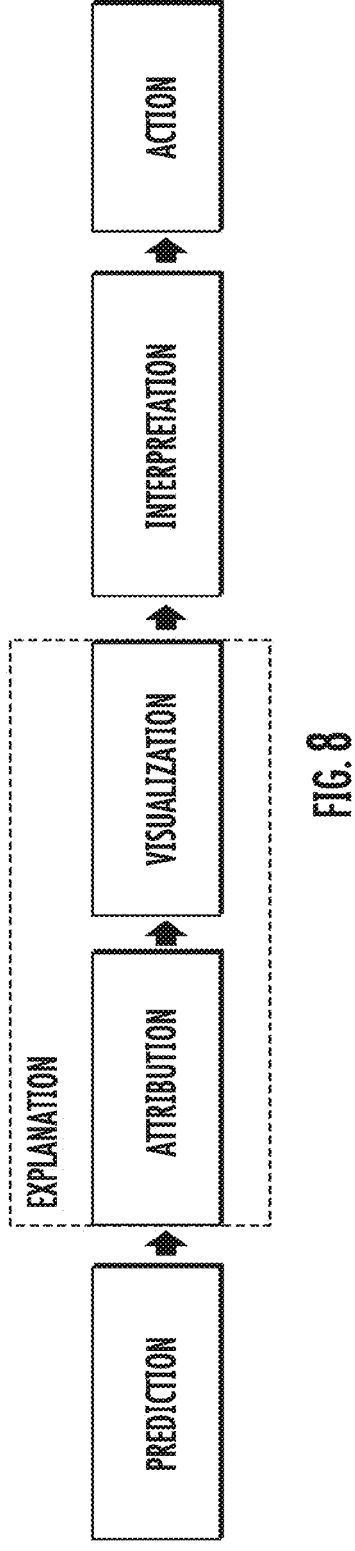
FIG. 8 depicts a flow diagram that describes the context surrounding the preparation of visualizations for the purpose of explaining how a neural network generates predictions.

A key feature of attribution-based explanations is the ability to express the attributions in a comprehensible manner suitable for human consumption. A common way to communicate attributions is by displaying the attributions themselves as a visualization. FIG. 8 depicts a flow diagram that describes the context surrounding the preparation of visualizations for the purpose of explaining how a neural network generates predictions. Because an individual will normally consume the visualization rather than the attribution values, the visualization should not distort the attribution values in a way that undermines the justifications underlying the attribution method. However, transforming the attribution values into a comprehensible visualization that remains faithful to the underlying justifications of the attribution method is not trivial.

Visualizations can be used in a variety of ways. For example, visualizations can be used by developers to debug the neural network. As another example, visualizations can be used by medical professionals to make diagnostic decisions. For instance, the neural network and explanation (e.g., in the form of a visualization representative of the attribution values) may be used to screen cases for review by the medical professional, or to assist the medical professional in rendering diagnoses. To accomplish these tasks, it is helpful to ensure that the medical professional comprehends the explanation.

There are at least three reasons why an individual may find it difficult to understand the explanation of a neural network. First, the neural network may reason differently than the individual. Second, the attribution method may distort the neural network's operation. Third, the visualization may distort the underlying attribution values (also referred to as "or "attribution measures" or "attributions").

In general, uncluttered visualizations tend to be easier to comprehend. Consider, for example, the difference between a scatter plot and a bar chart. The former displays a detailed relationship between two variables, but it can be relatively cluttered when a large number of values are displayed. The latter is relatively uncluttered and reduces the cognitive load needed for comprehension. However, it is possible that "binning" (e.g., of values along the x-axis of the bar chart) may hide relevant information. Ideally, a visualization should have minimal clutter without hiding information or causing artifacts.

If a visualization is cluttered, an individual may ignore the explanation altogether. This phenomenon is known as "disuse." Conversely, if a visualization is over-optimized for human consumption, this could result in selective suppression of interesting instances where the neural network and individual reach different conclusions (or even the same conclusion) by reasoning differently. This phenomenon is known as "misuse." Because disuse and misuse harm the overall accuracy of decision making, the diagnostic platform described herein have been designed to create visualizations with reduced clutter that do not cause confirmation bias.

Another aspect of producing a comprehensible visualization of an explanation depends on how well the visualization establishes a correspondence between the two layers of information, namely the input (e.g., an image) and the visualization of the attributions. Naively overlaying the attributions on top of the image may obscure interesting characteristics of the image, while visualizing these layers separately causes the correspondence between the explanation and the image to be lost. Generally, each visualization produced by a diagnostic platform satisfies four principles: graphical integrity, coverage, morphological clarity, and layer separation. Each of these principles is discussed below.

I. Graphical Integrity

One goal of the diagnostic platforms described herein is to have the visualizations represent the attributions as faithfully as possible. That is, visualizations produced by a diagnostic platform should actually reflect the underlying attributions. This concept is referred to as "graphical integrity." Intuitively, if a feature has twice the attribution of another, then it should appear twice as bright in the visualization. But this is quite difficult to achieve with precision, partly because perception of brightness is known to be non-linear and partly because there are spatial effects that affect perception.

A corollary to graphical integrity is that features with positive or negative attributions should be called out differently. This can be achieved rather easily, for example, by using different colors to display positive and negative attributions. However, the diagnostic platform should avoid naively translating "importance" in terms of high attribution magnitude by ignoring the sign of the attribution. This can be dangerous since the explanation can appear to lack sensitivity to the neural network (e.g., the attributions from two different neural networks may appear similar).

One way to achieve graphical integrity is for a diagnostic platform to linearly transform the attributions to the range [0, 255], where the maximum attribution magnitude is assigned a value of 255 in an 8-bit red-green-blue (RGB) space. The diagnostic platform may perform this transformation separately for positive and negative attributions such that positive attributions can be shown in one color (e.g., green) and negative attributions can be shown in another color (e.g., red).

Figures 9A, 9B, 9C, 9D, 9E:
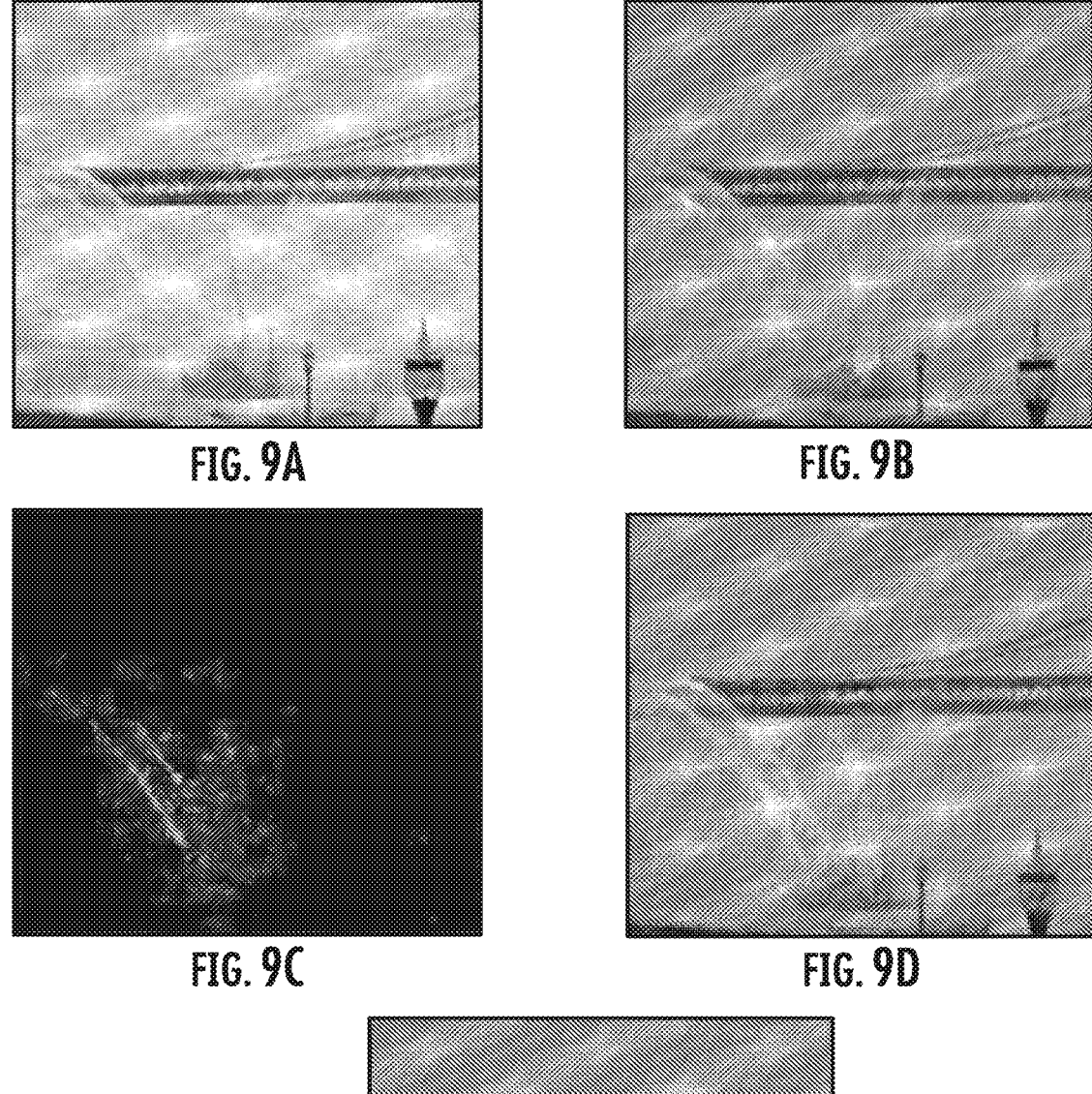
FIG. 9A depicts an example of an image to which a neural network designed for object recognition can be applied.
FIG. 9B depicts a "naïve" visualization in which the positive attributions have been linearly transformed to the range [0, 255] in the 8-bit red-green-blue (RGB) space.
FIG. 9C depicts the same naïve visualization overlaying a black background for additional clarity.
FIG. 9D depicts an example of a visualization in which a larger fraction of attributions are visible.
FIG. 9E depicts an example of a visualization in which pixels with negative attributions (in red) co-occur with pixels with positive attributions (in green).

As an example, consider the image shown in FIG. 9A. When a neural network designed for object recognition is applied to this image, the prediction is "fireboat." Attribution for the prediction has been computed by applying an attribution model with a black image as the baseline, and then a visualization is produced based on the positive attributions. FIG. 9B depicts a "naïve" visualization in which the positive attributions have been linearly transformed to the range [0, 255] in the 8-bit RGB space. The naïve visualization highlights some features that match the semantic understanding of the prediction. FIG. 9C depicts the same naïve visualization overlaying a black background for additional clarity. In FIGS. 9B-C, the visualization has primarily highlighted the water jets along the left side of the image. Note, however, that the water jets along the right side of the image, as well as the structure of the boat itself, are not highlighted.

Figure 10:
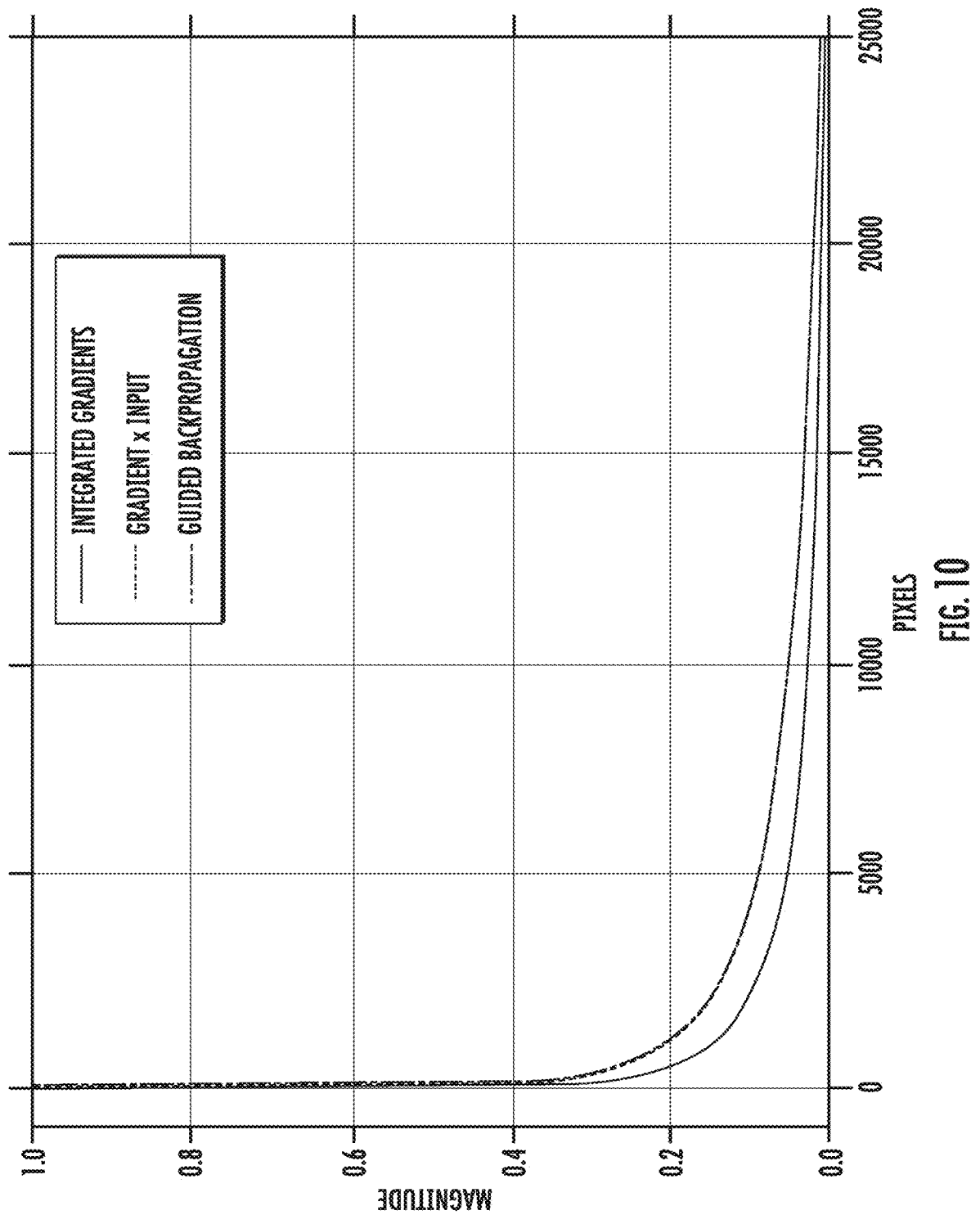
FIG. 10 includes an example distribution of attribution magnitude over pixels for three attribution methods—Integrated Gradients, Gradient×Input, and Guided Backpropagation.

Naïve visualizations may display only a small fraction of the total attribution. This is largely due to the fact that the attributions span a large range of values and are long-tailed. FIG. 10 includes an example distribution of attribution magnitude over pixels for three attribution methods—Integrated Gradients, Gradient×Input, and Guided Backpropagation. The large range implies that only the top few pixels by magnitude are highlighted, while the long tail implies that the invisible pixels hold the bulk of the attribution. In order to see 80 percent of the attribution magnitude, approximately 150,000 pixels would need to be visibly highlighted for a 1024×1024 image having 1,048,576 pixels. However, the naïve visualizations shown in FIGS. 9B-C have only visually highlighted approximately 500 pixels II. Coverage Consider the pixel with the kth max attribution value such that the top k pixels account for 75 percent of the attribution magnitude. Ideally, this pixel will be visible so as to cover the underlying features considered relevant to the output by the neural network. Now, suppose that the ratio of the max attribution value to the kth max attribution value is approximately 25. This would imply that if the max attribution value is close to 255 (e.g., in the 8-bit RGB space), then the kth max attribution value would be close to 10 (which is indistinguishable from black, and thus invisible). Accordingly, a diagnostic platform may impose a requirement that a large fraction of important features are visible in visualizations. This concept is referred to as "coverage."

To fix coverage, the diagnostic platform can automatically reduce the range of attributions generated by the attribution model. This can be done in several different ways, though the simplest is to clip the attributions near the upper end of the range. Although such action will sacrifice graphical integrity near the upper end of the range, it will dramatically improve coverage. FIG. 9D depicts an example of a visualization in which a larger fraction of attributions are visible. Referring to the example above, suppose that attributions are clipped at the 99th percentile. The ratio of the maximum attribution value to the kth max attribution value would fall from approximately 25 to approximately 5. This would imply that if the max attribution value is close to 255 (e.g., in the 8-bit RGB space), then the kth max attribution value would be close to 50 (which is distinguishable from black, and thus visible). A high degree of coverage (e.g., 75 percent of attribution values) can be achieved by sacrificing the graphical integrity for a small fraction of pixels (e.g., the top 1 percent by attribution value). Although attributions near the upper end of the range have been clipped in this example, those skilled in the art will recognize that attributions could be clipped near the upper end of the range, the lower end of the range, or some combination thereof.

FIGS. 9B-D correspond to visualizations of pixels with positive attributions. However, some pixels may receive a negative attribution. The graphical integrity and coverage requirements will normally apply to visualizing negative attributions in a similar manner. However, pixels with negative attributions generally fall into one of two categories. First, these pixels may coincide with pixels having positive attributions as part of the same feature. For example, if the neural network performs edge detection, positive and negative attributions may occur on either side of the edge. Second, these pixels may be associated with a single feature. In this case, the feature may represent a "vote" against the prediction made by the neural network.

While the diagnostic platform may opt to show the second type of negative attribution, the diagnostic platform may choose not to show the first type of negative attribution to avoid redundancy. For example, in the case of the fireboat, pixels with negative attributions co-occur with pixels with positive attributions as shown in FIG. 9E. It may be difficult to know a priori whether negative attributions are redundant. Therefore, a diagnostic platform may initially show the positive and negative attributions and then suppress the negative attributions (or at least some of the negative attributions) responsive to determining that they are redundant.

Figure 11B:
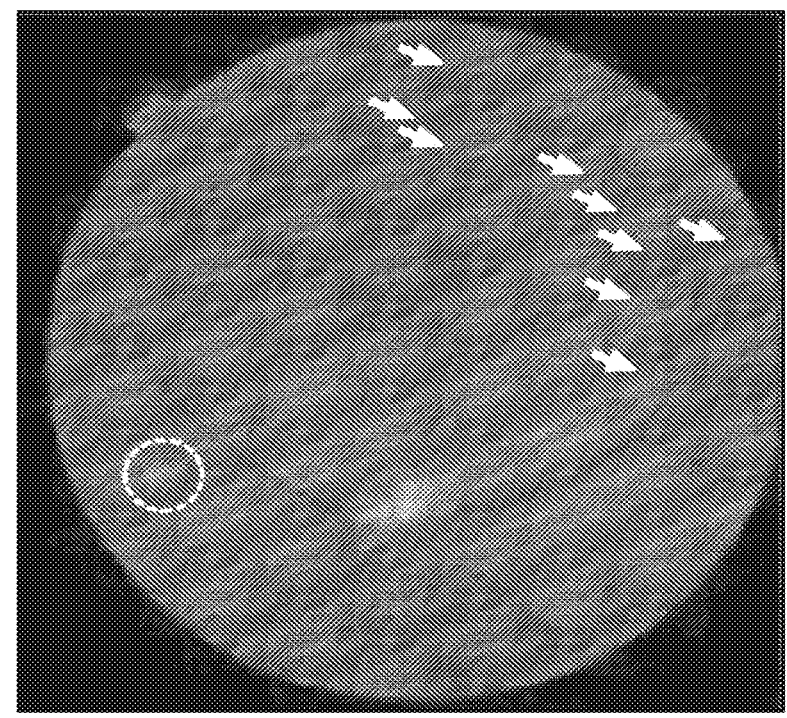
FIG. 11B depicts a visualization of the clipped range of attributions after being linearly transformed to the range [0, 255] in the 8-bit RGB space.
Figure 11A:
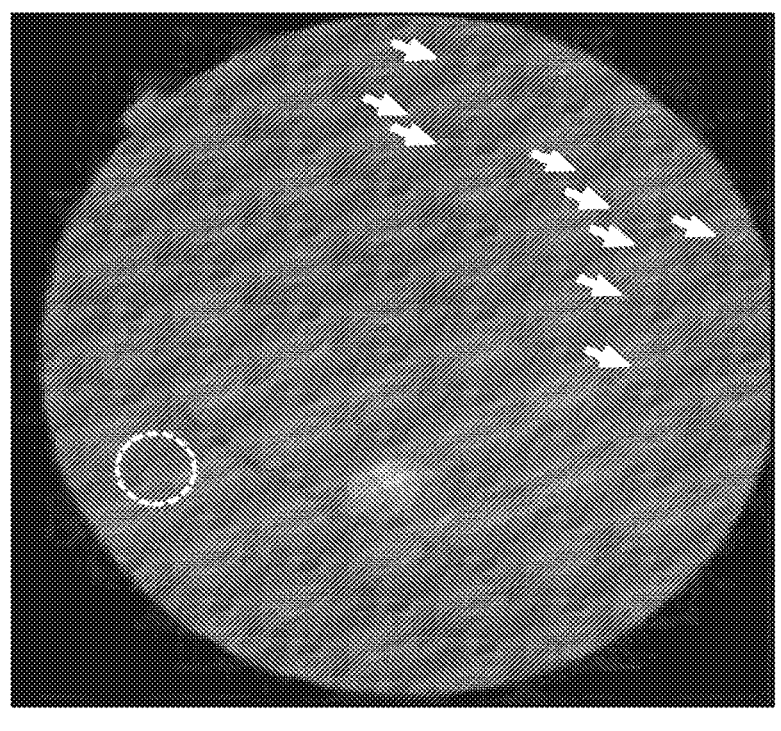
FIG. 11A depicts a naïve visualization of the entire range of attributions after being linearly transformed to the range [0, 255] in the 8-bit RGB space.

As noted above, neural networks have become increasingly popular for more critical tasks. For example, a diagnostic platform may apply a neural network trained to produce a prediction regarding diabetic retinopathy based on an analysis of a retinal image, and then the diagnostic platform may apply an attribution model to compute attributions indicating how the prediction relates to the retinal image. FIG. 11A depicts a naïve visualization of the entire range of attributions after being linearly transformed to the range [0, 255] in the 8-bit RGB space, while FIG. 11B depicts a visualization of the clipped range of attributions after being linearly transformed to the range [0, 255] in the 8-bit RGB space. Here, the attributions have been clipped below the 30th percentile value and above the 95th percentile value, though other thresholds may be used. The visualization of FIG. 11B has greater sensitivity for highlighting clinically-relevant features. For example, the visualization of FIG. 11A has missed features corresponding to hard exudates and microaneurysms outside of the optic disk.

The retinal image provided to the neural network as input was determined by a panel of medical professionals to have severe non-proliferative diabetic retinopathy. This determination was made by the panel of medical professionals based on features indicating specific types of pathology, such as microaneurysms, hemorrhages, and intra-retinal microvascular anomalies throughout the retinal image. Here, the neural network accurately predicted severe non-proliferative diabetic retinopathy based on the features discovered within the retinal image. While the naïve visualization highlights some of these features, it misses other features. For instance, many microaneurysm and hemorrhages have been omitted, particularly in the lower-right quadrant of the retinal image (as shown with the arrows in FIGS. 11A-B). Moreover, while the intra-retinal microvascular anomalies have been somewhat highlighted (as shown with the dotted circle in FIGS. 11A-B), it has relatively low salience in the naïve visualization. In contrast, the clipped visualization has highlighted these clinically-relevant features in a much more comprehensible manner.

III. Morphological Clarity

As discussed above, a visualization produced by a diagnostic platform must ultimately be designed for consumption by an individual responsible for interpreting the visualization. Because neural networks may behave in a manner that does not naturally result in coherence, it is important that the diagnostic platform produces visualizations that have a clear form (e.g., are not "noisy"). This concept is referred to as "morphological clarity" or "coherence."

Optimizing for morphological clarity may be done at the cost of faithfully representing the attributions. However, visualizations that satisfy morphological clarity are more effective in assistive contexts. To improve the coherence, a diagnostic platform may apply two morphological transformations. First, the diagnostic platform may fill in small holes in the attributions as part of a process called "closing." Second, the diagnostic platform may remove small, stray, and/or noisy features from the visualization as part of a process called "opening." These morphological transformations are described by Jean Serra in "Image Analysis and Mathematical Morphology," *Academic Press* (1983). FIG. 12 illustrates how these morphological transformations can be applied to the attributions produced by an attribution model. These morphological transformations reduce visual clutter, thereby improving coherence.

IV. Layer Separation

Visualizations establish correspondence between the attributions and the image considered as input by a neural network, so the attributions can highlight the feature(s) deemed important to the prediction produced by the neural network. In some embodiments, the image is processed by the diagnostic platform before the neural network is applied. For example, the diagnostic platform may remove artifacts, vary the coloration, crop pixels, etc. In other embodiments, the diagnostic platform does not process the image before the neural network is applied. Thus, the neural network can be applied to processed images and unprocessed images (also referred to as "raw images").

It is important that correspondence is established without occluding the image because the individual responsible for examining the attributions may want to inspect the image to verify the attributions, form a fresh opinion, etc. Accordingly, both layers of information, namely the attributions and the image, should be separately visible. This concept is referred to as "layer separation."

As shown in FIGS. 9B, 9D-E, 11A-B, and 12, visualizations representative of the attributions can be overlaid on the image or a version of the image (e.g., the image in grayscale format). In FIG. 12, for example, visualizations have been overlaid on top of a grayscale version of the image to ensure that the colors of the attribution do not collide with those of the image.

FIG. 13 illustrates an example scenario in which a diagnostic platform applies an attribution model to the prediction generated by a neural network (here, a severity grade for diabetic retinopathy), examines the matrix of attribution values generated by the attribution model to identify the pixels that exceed a specified threshold, and creates a visualization that visually highlights the identified pixels.

The specified threshold may be based on the desired sensitivity of the explanation. Considering only those pixels whose attribution values exceed the specified threshold will ensure that the visualization is based on pixels corresponding to diagnostically-relevant features.

As discussed above, the diagnostic platform may apply the attribution model to multiple predictions generated by a multi-headed neural network. In such embodiments, the diagnostic platform may produce a visualization that visually distinguishes the pixels considered relevant for each prediction. One example of such a visualization is a multivariable heatmap in which the pixels considered relevant to a first prediction are rendered in a first color, pixels considered relevant to a second prediction are rendered in a second color, etc. In some embodiments, the visualization is interactive. For example, the diagnostic platform may allow an individual to readily toggle between multiple heatmaps that, when overlaid on one another, appear as a multi-variable heatmap. As another example, the diagnostic platform may allow an individual to readily toggle between the image considered as input by the neural network, a version of the image (e.g., in grayscale format), the visualization explaining the neural network's rationale, and/or the underlying attribution values generated by the attribution model.

Figure 14B:
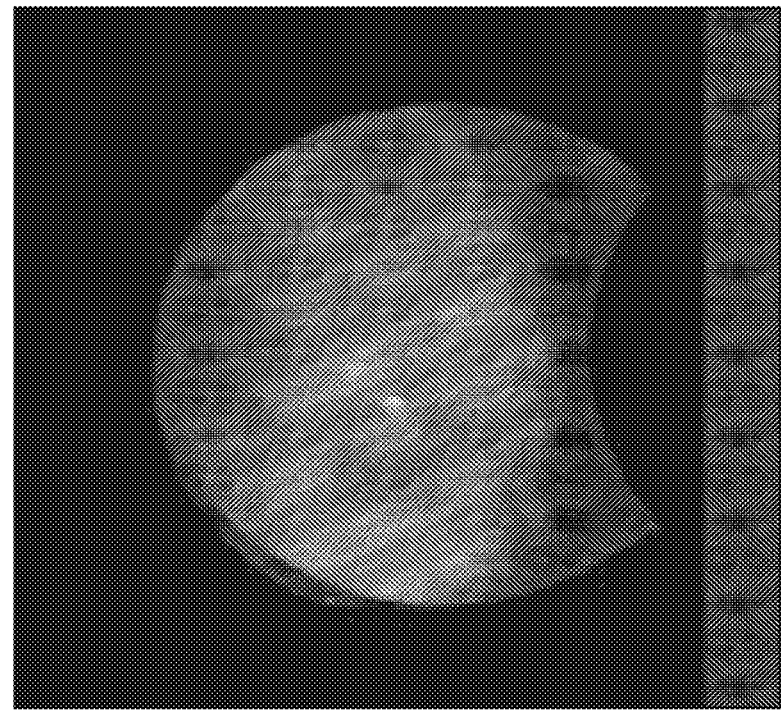
FIGS. 14A-N are examples of retinal images, modified versions of retinal images, and visualizations corresponding to those retinal images.
Figure 14A:
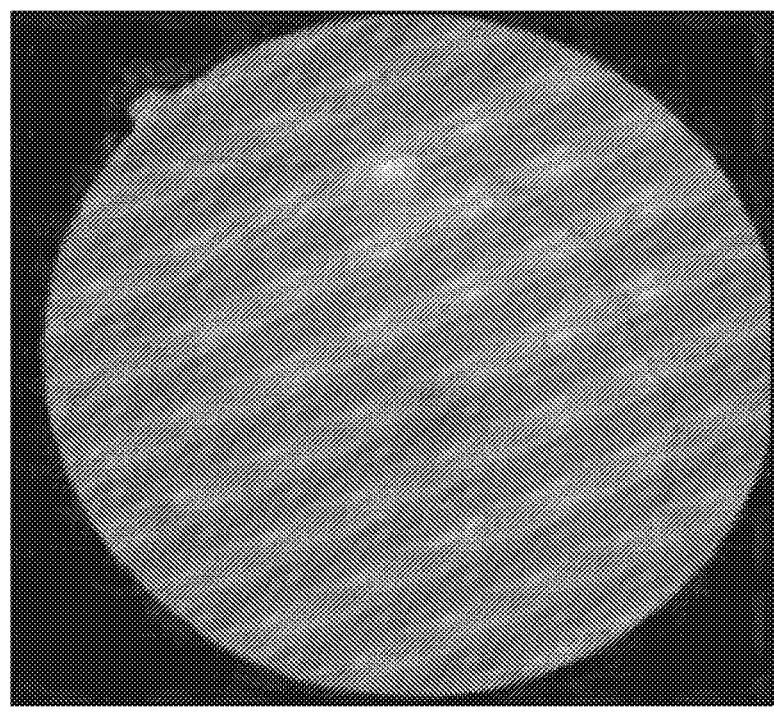
Figure 14F:
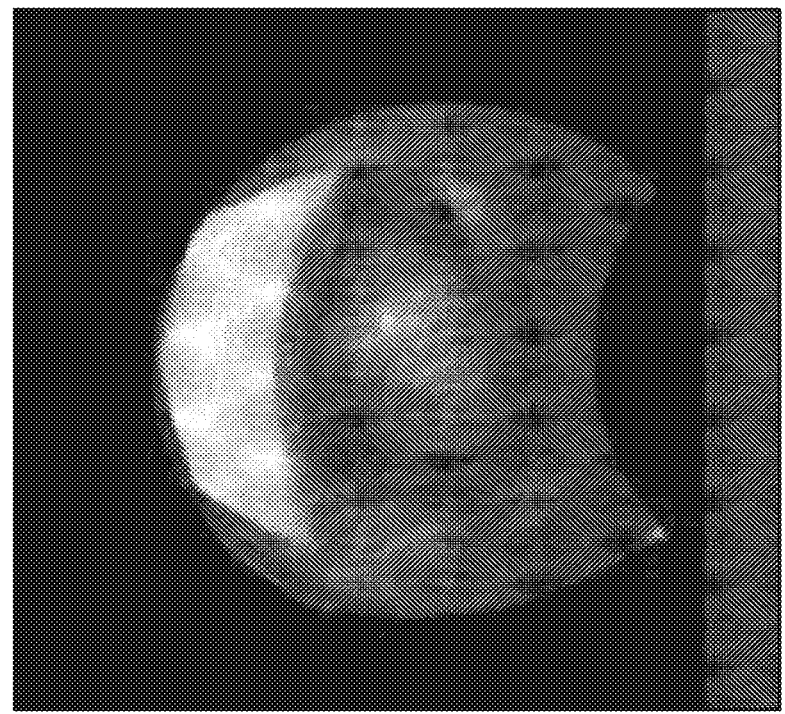
Figure 14E:
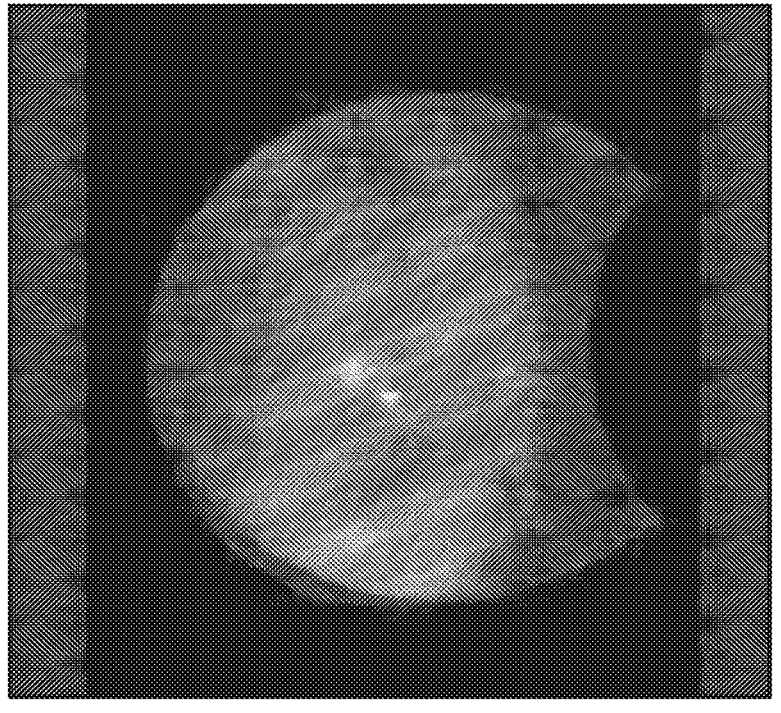
Figure 14H:
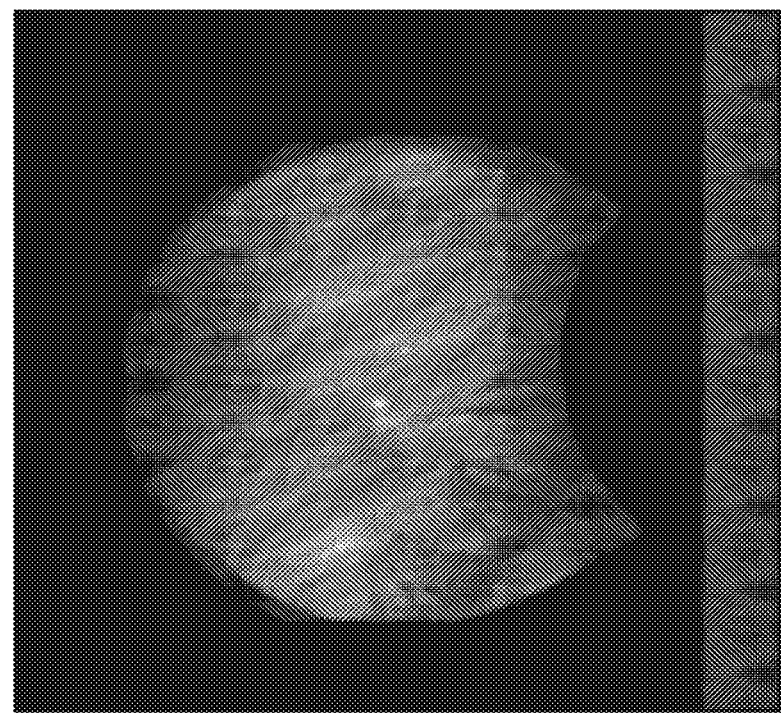
Figure 14G:
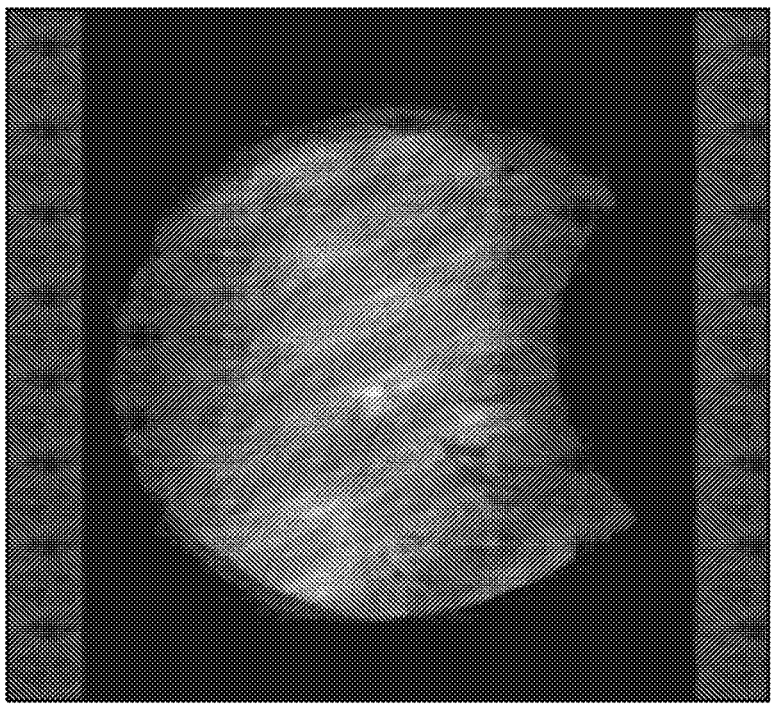
Figure 14J:
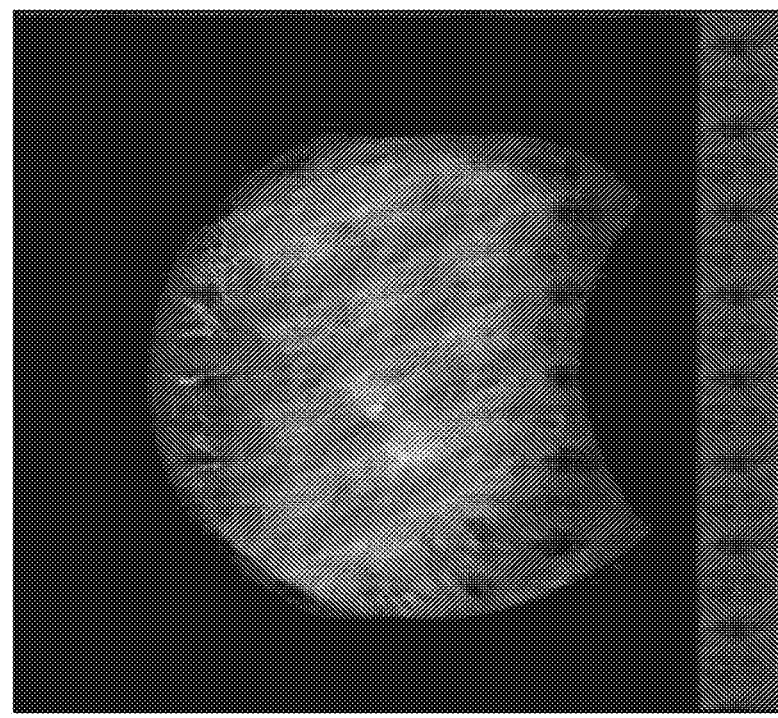
Figure 14I:
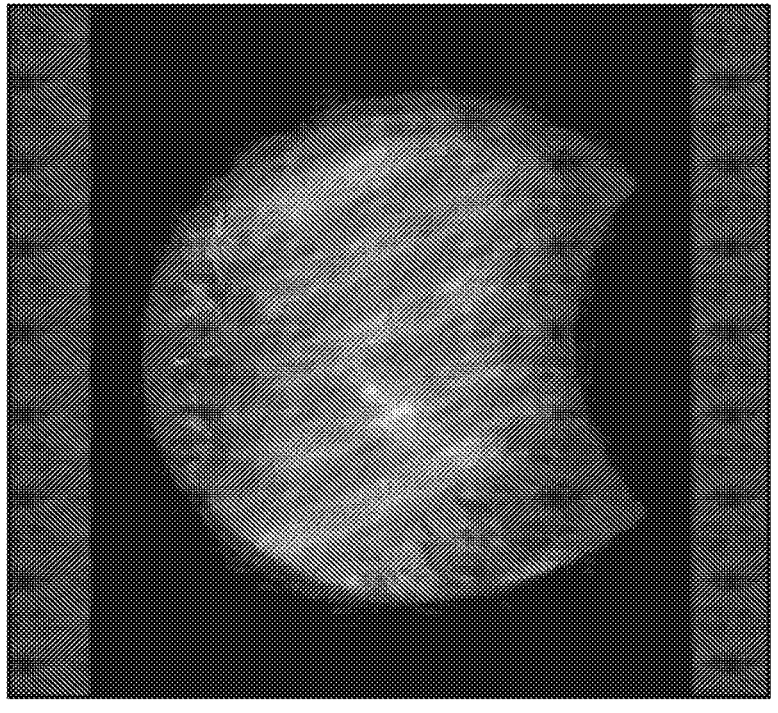
Figure 14L:
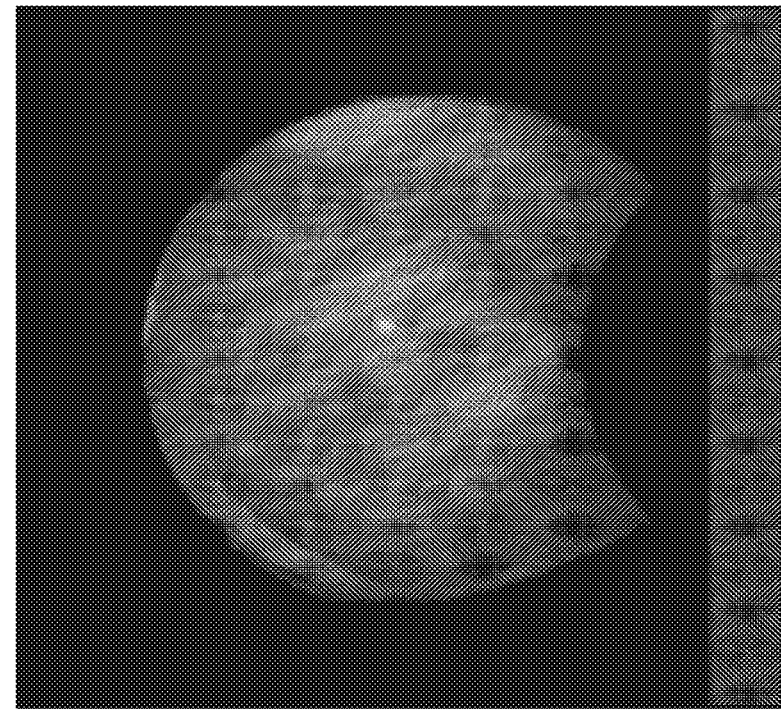
Figure 14K:
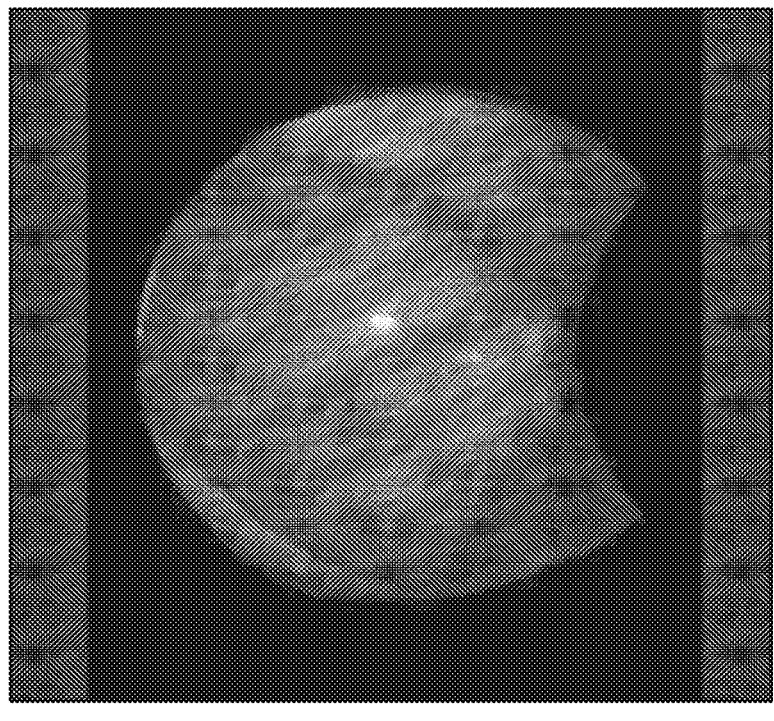
Figure 14N:
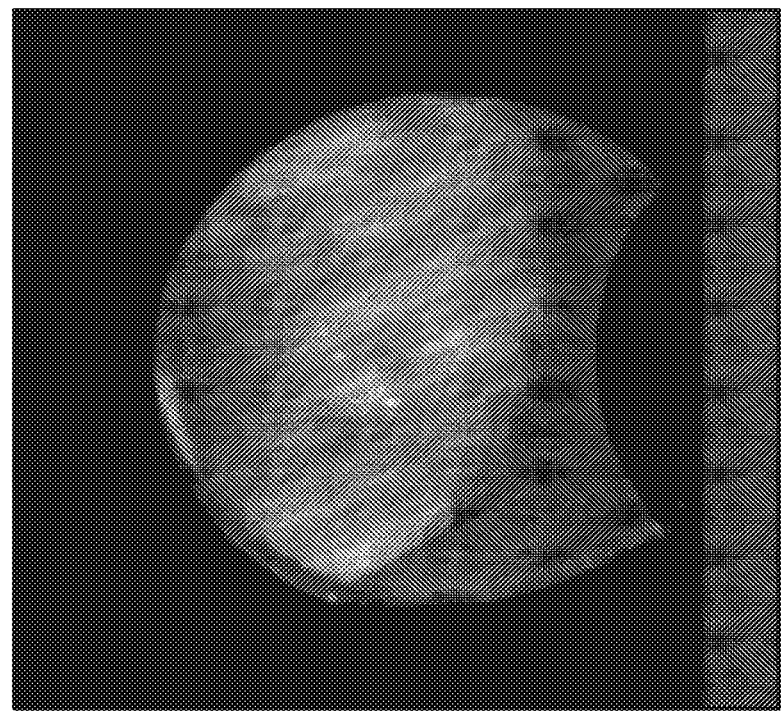
Figure 14M:
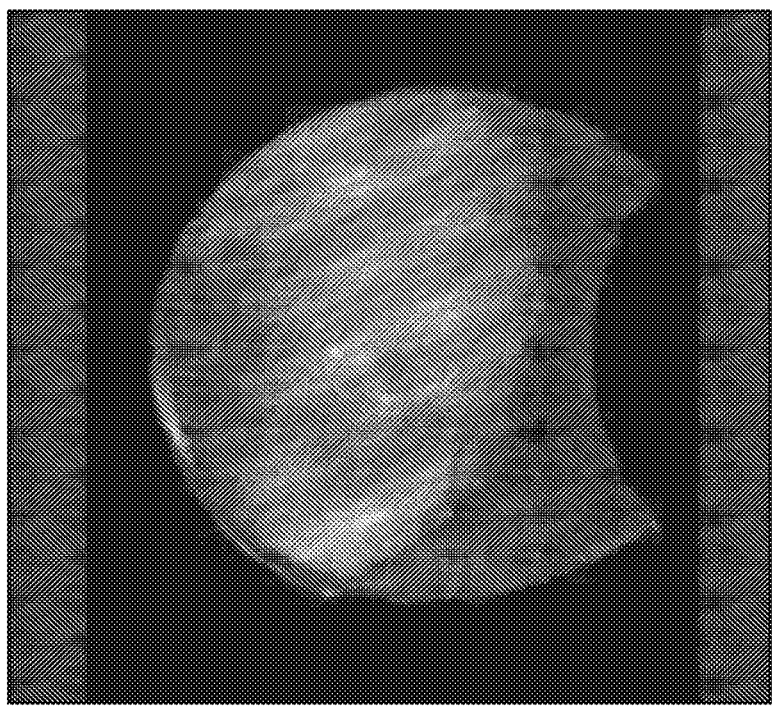

FIGS. 14A-N are examples of retinal images, modified versions of retinal images, and visualizations corresponding to those retinal images. FIG. 14, for example, is an example of a visualization in which the pixels deemed relevant to a prediction generated by a neural network have been outlined rather than rendered in a specific color. This may be useful to reduce clutter. For instance, if the diagnostically-relevant pixels are outlined, then the individual responsible for considering the prediction will be able to simultaneously view the corresponding segment of the image considered by the neural network. In some embodiments, the diagnostic platform thresholds the attribution values into a binary mask, where all non-zero attribution values are mapped to one and the remaining attribution values are mapped to zero. In other embodiments, the diagnostic platform thresholds the attribution into a binary mask, where all positive-magnitude attribution values are mapped to one and the remaining attribution values are mapped to zero. Then, the diagnostic platform can subdivide the mask into clusters by computing the connected components of the mask. For example, the diagnostic platform may rank the components by the sum of attribution weight inside each component and then keep the top "N" components. Finally, the diagnostic platform can establish the border around each kept component by subtracting the opening of the component by the component.

FIGS. 14B and 14D, meanwhile, are examples of modified versions of retinal images (here, converted into grayscale) with single-variable heatmaps laid thereon. FIGS. 14G-H, 14I-J, 14K-L, and 14M-N represent pairs of retinal images and corresponding visualizations.

FIG. 15 depicts a flow diagram of a process 1500 for producing a visualization to explain how a neural network generated a prediction based on an image. Initially, the diagnostic platform can acquire an image and a prediction made by the neural network based on the image (step 1501). The prediction may be made by the diagnostic platform as discussed above with respect to FIGS. 6-7. One example of a prediction is a proposed diagnosis for a medical condition.

The diagnostic platform can apply an attribution model to the prediction made by the neural network to produce an attribution value for each pixel in the image (step 1502). The attribution model may be programmed to estimate the contribution of each pixel in the image to the output based on a comparison to a corresponding pixel of a baseline image. In some embodiments, the diagnostic platform is configured to form a matrix of attribution values produced by the attribution model (step 1503). The matrix of attribution values will generally have the same dimensions as the image considered as input by the neural network. For example, a 1024×1024 matrix can be created with a separate entry for each pixel in a 1024×1024 image. The attribution value associated with each pixel is indicative of the impact that pixel had on the prediction produced by the neural network.

Thereafter, the diagnostic platform can examine the matrix of attribution values to identify pixels whose attribution values exceed a threshold (step 1504). For example, in some embodiments the diagnostic platform identifies all pixels associated with non-zero attribution values, while in other embodiments the diagnostic platform identifies all pixels associated with attribution values exceeding 0.1, 0.3, or 0.5 on a normalized scale. Then, the diagnostic platform can create a visualization that visually distinguishes the identified pixels from other pixels in the image (step 1505). As discussed above, this can be accomplished in a variety of different ways.

FIG. 16 depicts a flow diagram of another process 1600 for producing a visualization to explain how a neural network generated a prediction based on an image. Steps 1601-1602 of FIG. 16 are similar to steps 1501-1502 of FIG. 15. Here, however, the diagnostic platform is configured to arrange the attribution values produced by the attribution model by magnitude (step 1603). Such action allows the diagnostic platform to filter the attribution values so that all attribution values exceeding a given percentile are clipped (step 1604). For example, the diagnostic platform may clip attribution values above the 99th percentile, 97th percentile, 95th percentile, etc. Additionally or alternatively, the diagnostic platform may filter the attribution values so that all attribution values falling below a given percentile are clipped. For example, the diagnostic platform may clip attribution values below the 5th percentile, 10th percentile, or 20th percentile.

The diagnostic platform can transform the filtered attribution values into a color space suitable for display on computing devices (step 1605), and then create a visualization based on the transformed attribution values (step 1606). For example, the diagnostic platform may transform the filtered attribution values into the 8-bit RGB space. In such embodiments, the filtered attribution values can be transformed to the range [0, 255], where the maximum filtered attribution value is assigned a value of 255. As discussed above, the attribution model can produce a separate series of attribution values for each prediction made by the neural network based on the image. Each series of attribution values may be assigned to a different color for visualization purposes. For example, the attribution values corresponding to a first prediction may only be assigned a value in the red color channel, while the attribution values corresponding to a second prediction may only be assigned a value in the green color channel.

FIG. 17 depicts a flow diagram of a process 1700 for outlining clusters of pixels determined to be diagnostically relevant to a prediction made by a neural network. Initially, a diagnostic platform can acquire attribution values produced by an attribution model that was applied to a prediction made by a neural network (step 1701). The diagnostic platform may have applied the attribution model to the prediction as discussed above with respect to FIGS. 6-7 and 15.

The diagnostic platform can compute a binary mask from the attribution values (step 1702). More specifically, the diagnostic platform can threshold the attribution values into a binary mask, where all non-zero attribution values are mapped to one and the remaining attribution values are mapped to zero. In some embodiments, the diagnostic platform fills in small holes in contiguous regions of attribution values included in the binary mask (step 1703). This process is commonly called "closing." Similarly, the diagnostic platform may remove small, stray, and/or noisy regions of attribution values included in the binary mask (step 1704). This process is commonly called "opening."

Then, the diagnostic platform can subdivide the binary mask into connected components (also referred to as "clusters of pixels") by discovering the connected components of the binary mask (step 1705). In some embodiments, the diagnostic platform ranks the connected components by the sum of attribution weight inside each connected component and then keeps the top "N" components. That is, the diagnostic platform may sum the attribution scores within each connected component to identify each connected component that makes up at least a certain percentage of the entire sum of attribution scores (step 1706). For example, the diagnostic platform may only retain those connected components whose pixels make up at least one percent of the entire sum of attribution scores. Such action enables the diagnostic platform to produce visualizations in which every diagnostically-relevant pixel is not visually distinguishable. Finally, the diagnostic platform can create a visualization in which a border is drawn around each identified connected component by subtracting the opening of the connected component by the connected component (step 1707).

Diagnostic Platform Workflow

Explaining how neural networks produce outputs is an important aspect in developing a diagnostic platform able to meaningfully contribute to a computer-aided diagnostic process. For example, the diagnostic platform may be designed to produce explanatory visualizations that allow an individual (e.g., a medical professional) to "see" which features the neural network determined were diagnostically relevant. As the complexity of requests for these visualizations increases, however, the workflow of the diagnostic platform must be modified.

FIG. 18 illustrates how information may flow between a series of computer servers able to produce predictions indicative of proposed diagnoses. Initially, a computer-aided diagnostic (CADx) computer server will receive input from a computing device indicative of a request to generate a prediction based on an image. The computing device may be a mobile phone, desktop computer, or mobile workstation. Generally, the computing device is accessible to a medical professional responsible for examining the image.

Upon receiving the input, the CADx computer server can request that inference be separately performed at least twice for the image. Here, for example, the CADx computer server has submitted a separate request for classification results to two separate Inference Server instances (i.e., Inference Server Instance 1 and Inference Server Instance 2). Note, however, that the request could be submitted to any number of instances. As discussed above, to produce a classification result (e.g., a prediction indicative of a proposed diagnosis), each instance can apply a diagnostic model to the image acquired by the CADx computer server. Each instance can then return a classification result as determined by the diagnostic model to the CADx computer server.

The CADx computer server can compare the classification results received from the instances. If the classification results are sufficiently similar (e.g., identical diagnoses), then the CADx computer server can transmit the classification result to the computing device. However, if the classification results are not sufficiently similar (e.g., dissimilar diagnoses), then the CADx computer server may generate an error notification. The error notification may prompt the CADx computer server to resubmit the inference request to the instances, submit the inference request to another instance that wasn't previously involved in the workflow, etc.

While the workflow shown in FIG. 18 is suitable for handling requests to produce classification results, the instances can become overwhelmed if the requests to produce classification results are accompanied by requests to produce visualization results (e.g., in the form of explanatory visualizations). To support the visualization technologies described above, additional instances dedicated to this task can be spun up.

Figure 19:
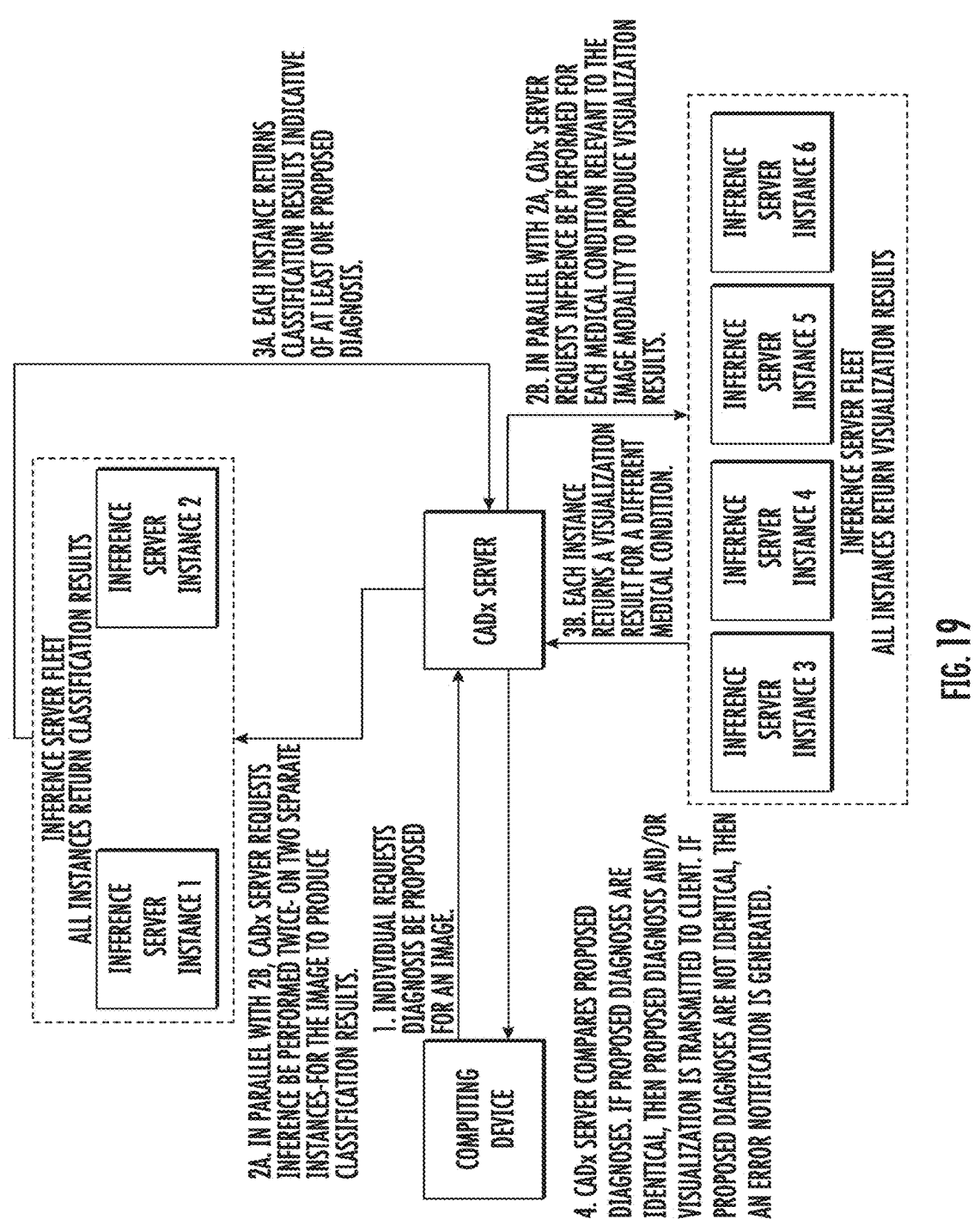
FIG. 19 illustrates how the computer-aided diagnostic (CADx) computer server can make requests to instances for classification results (e.g., predictions indicative of proposed diagnoses) in parallel with requests to instances for visualization results.

FIG. 19 illustrates how the CADx computer server can make requests to instances for classification results (e.g., predictions indicative of proposed diagnoses) in parallel with requests to instances for visualization results. Here, the CADx computer server submit requests for classification results to a first set of instances (e.g., Inference Server Instance 1 and Inference Server Instance 2) and requests for visualization results to a second set of instances (e.g., Inference Server Instance 3, Inference Server Instance 4, Inference Server Instance 5, and Inference Server Instance 6). Note, however, that the number of instances in each set could vary.

For instance, as discussed above, the CADx computer server can submit a request for classification results to the first set of instances. Each instance can generate classification results by applying a diagnostic model to an input such as an image. The diagnostic model may be represented by a neural network designed to generate a prediction for at least one medical condition. As shown in FIG. 19, the CADx computer server can submit a separate request for visualization results for each medical condition for which the neural network will generate a prediction. Accordingly, the number of instances in the second set may vary. For example, if each instance in the first set applies a single-headed neural network to produce a single prediction, then a single visualization result is needed. In such a scenario, the second set may include a single instance. However, if each instance in the first set applies a multi-headed neural network to produce multiple predictions, then multiple visualization results are needed. In such a scenario, the second set may include multiple instances, and each instance of the multiple instances may produce visualization results for a different prediction generated by the multi-headed neural network.

Because the requests can be submitted in parallel, the CADx computer server can monitor whether a visualization is necessary throughout the workflow in real time. For example, as soon as the classification results are received from at least one instance in the first set of instances, the CADx computer server can determine whether cancellation of the requests for visualization results is appropriate. Cancellation of a request for visualization results may be appropriate if the classification results indicate that no disease is present, or if the classification results indicate that the image was ungradeable.

This change in the workflow reduces the latency of requests as perceived by the individuals responsible for requesting the proposed diagnosis through the electronic device. Other modifications to the workflow could be made to reduce perceived latency.

For example, the CADx computer server may check to see whether classification results already exist for an image. In particular, when the CADx computer server receives a request to generate a proposed diagnosis, the CADx computer server can determine whether classification results already exist for the image. Past classification results may be stored in a profile associated with the individual captured in the image, the imaging device responsible for capturing the image, an entity (e.g., a hospital or clinic) involved in the diagnostic session, or a version of the diagnostic model.

As another example, the CADx computer server may preemptively compute the classification and visualization results as soon as ingestion of the image has completed. That is, the CADx computer server may produce the classification and visualization results before receiving an explicit request to do so from the computing device. The CADx computer server may identify the appropriate diagnostic model(s) based on content of the image, metadata that accompanies the image, etc. For instance, the CADx computer server may request that the first set of instances apply a diagnostic model corresponding to diabetic retinopathy responsive to determining that the image is a retinal image. Individuals may be able to toggle whether the CADx computer server preemptively computes the classification and visualization results. Moreover, individuals may be able to toggle which diagnostic models can be preemptively applied.

Other workflows may be desirable in some instances. For example, the CADx computer server could sequentially submit requests for visualization results to the second set of instances after submitting the requests for classification results to the first set of instances. This workflow would be les wasteful from a compute-resources perspective than the workflow shown in FIG. 19 if the classification result were negative (i.e., no disease is present).

Figure 20:
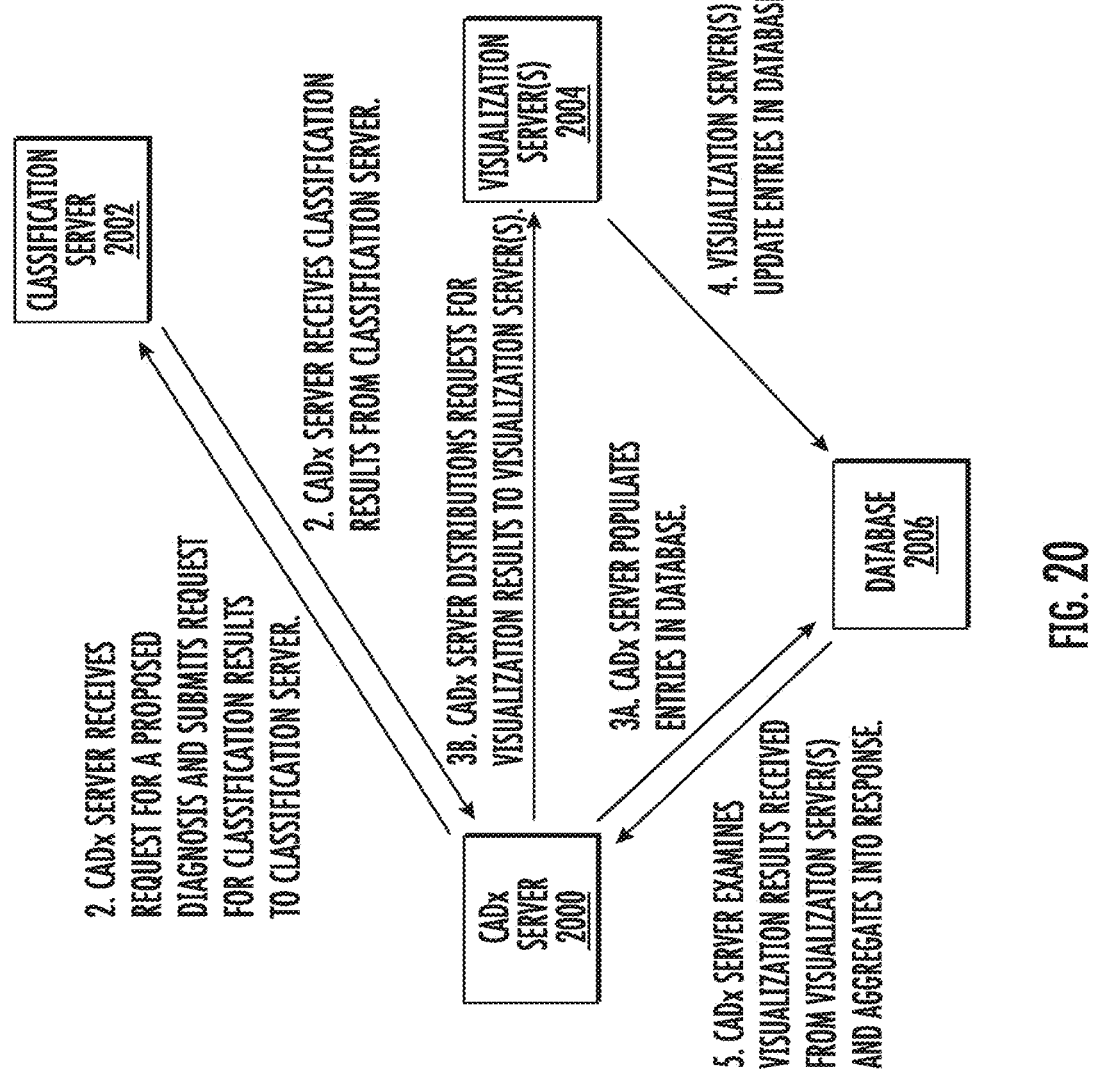
FIG. 20 depicts an example of a network environment that includes a CADx computer server, a classification computer server, one or more visualization computer servers, and a database.

FIG. 20 depicts an example of a network environment that includes a CADx computer server 2000, a classification computer server 2002, one or more visualization computer servers 2004, and a database 2006. As discussed above, the CADx computer server 2000 can submit a request for classification results to a classification server 2002. The classification server 2002 can generate the classification results by applying a neural network designed to generate a prediction for at least one medical condition. Moreover, the CADx computer server 2000 can submit a request for visualization results for each medical condition to a different visualization server 2004. As discussed above, the CADx computer server 2000 may submit these requests to the classification and visualization servers 2002, 2004 simultaneously.

As requests for visualization results are being transmitted to the visualization computer servers 2004, the CADx computer server 2000 may populate entries in the database 2006. Each entry in the database 2006 may be associated with a medical condition. Thus, the CADx computer server 2000 may populate each entry with information regarding the corresponding medical condition (e.g., as derived from the classification or visualization results). The database may be a relational database system that employs a series of protocols to shard (i.e., partition) data across multiple computer servers. For instance, the database could shard data across tens or hundreds of computer servers.

Processing System

Figure 21:
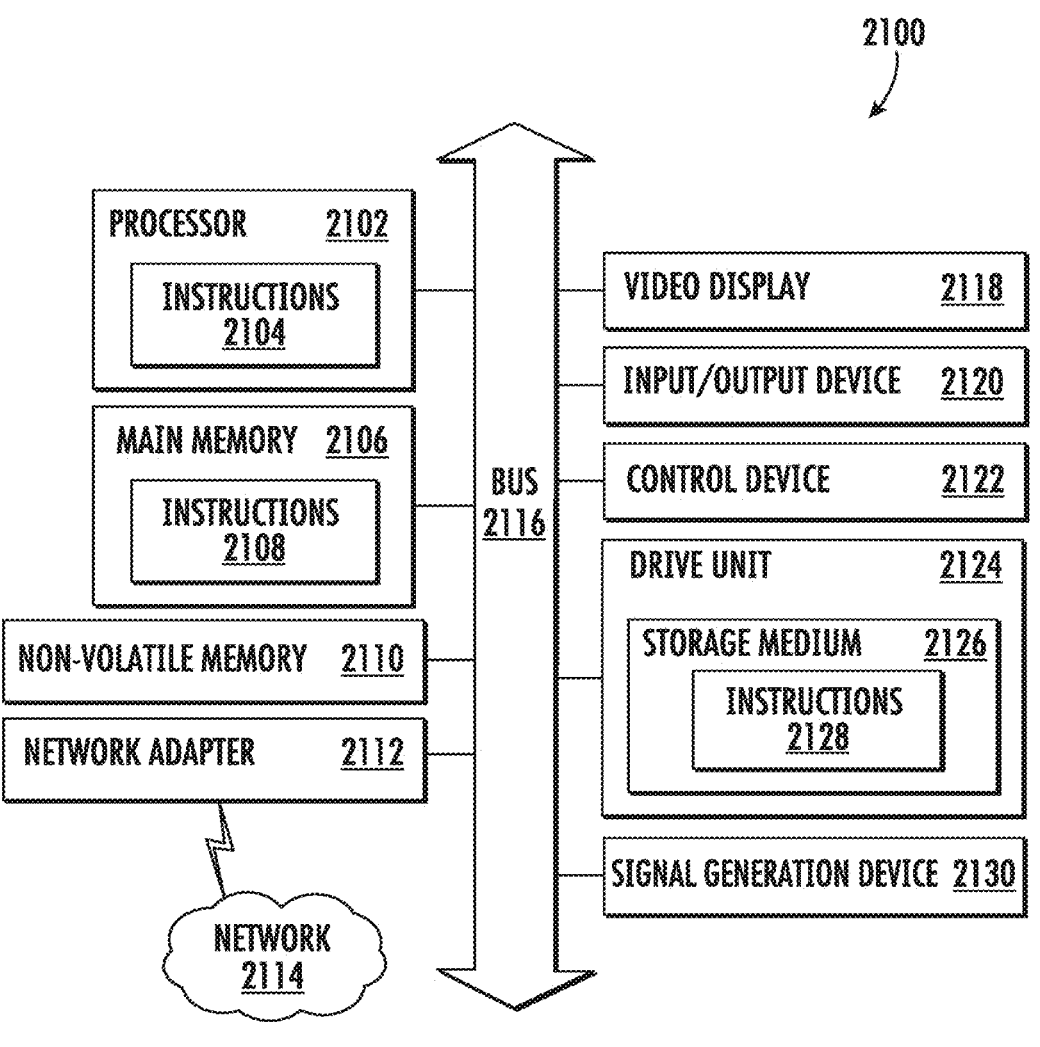
FIG. 21 is a block diagram illustrating an example of a processing system in which at least some operations described herein can be implemented.

FIG. 21 is a block diagram illustrating an example of a processing system 2100 in which at least some operations described herein can be implemented. For example, some components of the processing system 2100 may be hosted on a computing device that includes a diagnostic platform (e.g., diagnostic platform 302 of FIG. 3).

The processing system 2100 may include one or more central processing units ("processors") 2102, main memory 2106, non-volatile memory 2110, network adapter 2112 (e.g., network interface), video display 2118, input/output devices 2120, control device 2122 (e.g., keyboard and pointing devices), drive unit 2124 including a storage medium 2126, and signal generation device 2130 that are communicatively connected to a bus 2116. The bus 2116 is illustrated as an abstraction that represents one or more physical buses and/or point-to-point connections that are connected by appropriate bridges, adapters, or controllers. The bus 2116, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 2100 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 2100.

While the main memory 2106, non-volatile memory 2110, and storage medium 2126 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 2128. The term "machine-readable medium" and "storage medium" shall also be taken to include any medium that is capable of storing, encoding, or carrying a set of instructions for execution by the processing system 2100.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 2104, 2108, 2128) set at various times in various memory and storage devices in a computing device. When read and executed by the one or more processors 2102, the instruction(s) cause the processing system 2100 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 2110, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 2112 enables the processing system 2100 to mediate data in a network 2114 with an entity that is external to the processing system 2100 through any communication protocol supported by the processing system 2100 and the external entity. The network adapter 2112 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 2112 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
acquiring an image generated during a diagnostic session;
applying a diagnostic model associated with multiple different types of medical conditions to the image to produce multiple diagnoses,
   wherein upon being applied to the image, the diagnostic model employs a multi-headed neural network to produce multiple outputs indicating a separate diagnosis for each type of medical condition of the multiple different types of medical conditions;
determining contributions of pixels in the image to the multiple diagnoses produced by the multi-headed neural network by establishing contribution on a per-pixel and per-diagnosis basis;
identifying, based on an analysis of the contributions,
   a first set of pixels determined to have contributed to the production of a first diagnosis for a first type of medical condition, and
   a second set of pixels different from the first set of pixels and determined to have contributed to the production of a second diagnosis for a second type of medical condition; and
causing display, on an electronic device, of a single unified visualization of the image that includes modifications to both the first and second sets of pixels of the image to indicate a magnitude of the contributions of the first and second sets of pixels to the first and second diagnoses, respectively,
   wherein the modifications visually distinguish the first and second sets of pixels from each other and from other pixels in the image, and
   wherein the magnitude is positive or negative.

2. The computer-implemented method of claim 1,
wherein said determining comprises applying an attribution model to each diagnosis of the multiple diagnoses produced by the multi-headed neural network,
wherein the attribution model produces a matrix of attribution values for each diagnosis of the multiple diagnoses, and
wherein each attribution value is representative of the importance of the corresponding pixel to the corresponding diagnosis.

3. The computer-implemented method of claim 1, wherein the visualization causes the first and second sets of pixels to have different image characteristics.

4. The computer-implemented method of claim 1, wherein the electronic device is associated with a medical professional responsible for managing the diagnostic session.

5. The computer-implemented method of claim 1, wherein the first and second sets of pixels share at least one pixel in common.

6. The computer-implemented method of claim 1, wherein the image comprises a retinal image, and wherein the multiple different medical conditions comprise multiple ocular conditions.

7. A non-transitory computer-readable medium with instructions stored thereon that, when executed by a processor, cause the processor to perform operations comprising:

applying a diagnostic model associated with multiple different types of conditions to an image generated during a diagnostic session to produce multiple outputs, wherein each output of the multiple outputs is indicative of a corresponding one of the multiple different types of conditions, and wherein upon being applied to the image, the diagnostic model employs a multi-headed neural network to produce a separate output for each type of condition of the multiple different types of conditions;

applying an attribution model to each output of the multiple outputs produced by the multi-headed neural network, the attribution model being programmed to:

identify a reference image to serve as a baseline, and estimate the contribution of a given pixel in the image to a given output based on a comparison to a corresponding pixel of the reference image, wherein the attribution model produces a separate matrix of attribution values for each output of the multiple outputs;

determining, for each output of the multiple outputs, which pixels in the image were determined to contribute to the output by examining a corresponding matrix of attribution values;

transforming the corresponding matrix of attribution values to a range of values in a color space; and causing display of a single visualization of the image that includes modifications to the pixels in the image determined to contribute to each output of the multiple outputs according to the transformation, wherein the modifications visually distinguish the pixels in the image determined to contribute to each output from each other and from other pixels in the image.

8. The non-transitory computer-readable medium of claim 7, wherein each output of the multiple outputs is indicative of a proposed diagnosis for the corresponding type of condition.

9. The non-transitory computer-readable medium of claim 7, wherein the operations further comprise:

identifying a first set of pixels determined to have contributed to the production of a first output for a first type of condition, and a second set of pixels different from the first set of pixels and determined to have contributed to the production of a second output for a second type of condition, wherein causing display of a visualization of the image comprises causing display of the visualization that visually distinguishes the first and second sets of pixels from other pixels in the image on an electronic device.

10. The non-transitory computer-readable medium of claim 9, wherein the visualization is a multi-variable heatmap.

11. The non-transitory computer-readable medium of claim 10, wherein the operations further comprise:

creating multiple single-variable heatmaps by producing, for each output of the multiple outputs, a separate single-variable heatmap that visually distinguishes pixels in the image determined to have contributed to a corresponding type of condition of the multiple different types of conditions by the multi-headed neural network; and compiling the multiple single-variable heatmaps into the multi-variable heatmap.

12. The non-transitory computer-readable medium of claim 9, wherein the operations further comprise:

receiving input indicative of a selection of the first output; and causing display of a different visualization that visually distinguishes only the first set of pixels from the other pixels in the image on the electronic device.

13. The non-transitory computer-readable medium of claim 12, wherein the different visualization is a single-variable heatmap.

14. The non-transitory computer-readable medium of claim 7, wherein the operations further comprise:

storing the matrices of attribution values in a profile associated with an individual captured in the image.

15. An electronic device comprising:

a memory that includes instructions for producing multi-variable heatmaps to assist individuals in rendering diagnoses, wherein the instructions, when executed by a processor, cause the processor to:

acquire an image generated by an imaging device during a diagnostic session;

apply a multi-headed neural network to the image to produce a diagnosis for each medical condition of multiple different medical conditions, thereby producing multiple diagnoses;

determine a contribution of each pixel in the image to each diagnosis of the multiple diagnoses produced by the multi-headed neural network;

identify a first set of pixels determined to have contributed to the production of a first diagnosis, and a second set of pixels different from the first set of pixels and determined to have contributed to the production of a second diagnosis; and cause a multi-variable heatmap that includes modifications to colors of the first and second sets of pixels to be shown on a display, wherein the modifications are based on original values of the first and second sets of pixels, wherein the modifications visually distinguish the first and second sets of pixels from each other and from other pixels in the image, and wherein the modifications to the first and second sets of pixels of the image to indicate a magnitude of the contributions of the first and second sets of pixels to the first and second diagnoses.

16. The electronic device of claim 15, wherein the multi-variable heatmap overlays the image when shown on the display.

17. The electronic device of claim 15, wherein the instructions further cause the processor to:

receive input indicative of a selection of the first set of pixels or the first diagnosis; and cause display of a single-variable heatmap that visually distinguishes only the first set of pixels from other pixels of the image.

18. The electronic device of claim 15, wherein the instructions further cause the processor to:

receive input indicative of a selection of the first set of pixels or the first diagnosis; and cause the first set of pixels to be rendered at a higher intensity than the second set of pixels in the multi-variable heatmap.

19. The electronic device of claim 15, wherein the processor is communicatively coupled to the display across a network.

20. The electronic device of claim 15, wherein the processor is communicatively coupled to the imaging device across a network.

* * * * *